United States Patent [19]

Nagata et al.

[11] Patent Number: 5,496,843
[45] Date of Patent: Mar. 5, 1996

[54] TRICYCLIC INDOLE-2-CARBOXYLIC ACID DERIVATIVES

[75] Inventors: Ryu Nagata, Kyoto; Norihiko Tanno, Ibaraki; Nobuyuki Ae, Toyonaka, all of Japan

[73] Assignee: Sumitomo Pharmaceuticals Company, Limited, Osaka, Japan

[21] Appl. No.: 339,687

[22] Filed: Nov. 14, 1994

[30] Foreign Application Priority Data

Nov. 17, 1993 [JP] Japan ................................ 5-312742

[51] Int. Cl.$^6$ ........................ A61K 31/40; C07D 209/62
[52] U.S. Cl. .................................... 514/411; 548/436
[58] Field of Search ............................. 548/436; 514/411

[56] References Cited

FOREIGN PATENT DOCUMENTS

| 0383504 | 8/1990 | European Pat. Off. . |
|---|---|---|
| 0394905 | 10/1990 | European Pat. Off. . |
| 0483881 | 5/1992 | European Pat. Off. . |
| 2266091 | 10/1993 | United Kingdom . |
| 9201670 | 2/1992 | WIPO . |
| 9216205 | 10/1992 | WIPO . |
| 9220649 | 11/1992 | WIPO . |
| 9308188 | 4/1993 | WIPO . |
| 9413637 | 6/1994 | WIPO . |
| 9420465 | 9/1994 | WIPO . |

OTHER PUBLICATIONS

Gray et al., J. Med. Chem., 34, 1283–1292 (1991).
Salituro et al., Bioorganic & Medicinal Chemistry Letters, 1, (9), 455–460 (1991).
Salituro et al., J. Med. Chem., 33, 2944–2946 (1990).
Salituro et al., J. Med. Chem., 35, 1791–1799 (1992).
Uhle et al., J. Am. Chem. Soc., 77, 3334–3337 (1955).
Huettner, Science, 243, 1611–1613 (1989).
Leeson et al., J. Med. Chem., 36, 1954–1968 (1992).

Primary Examiner—Jacqueline Haley
Attorney, Agent, or Firm—Birch, Stewart, Kolasch & Birch

[57] ABSTRACT

A tricyclic indole-2-carboxylic acid derivative represented by the formula 1:

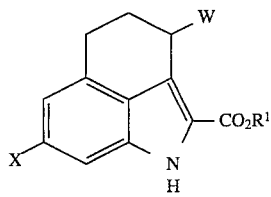

wherein
X represents alkyl, halogen or cyano;
$R^1$ represents hydrogen, or a protecting group of carboxyl group;
W represents hydrogen, —$CO_2R^{3i}$, —$CONR^{3i}R^{4i}$, —A—$CO_2R^{3i}$ or —A— $CONR^{3i}R^{4i}$, wherein —A— represents alkylene and $R^{3i}$ and $R^{4i}$ independently represent hydrogen, alkyl, aryl or substituted aryl,
or a pharmaceutically acceptable salt thereof, these compounds are selective antagonists of glycine binding site of the NMDA receptor.

19 Claims, No Drawings

TRICYCLIC INDOLE-2-CARBOXYLIC ACID DERIVATIVES

FIELD OF INVENTION

This invention relates to a new class of tricyclic indole-2-carboxylic acid derivatives which are selective antagonists of glycine binding site of the NMDA (N-methyl-D-aspartate) receptor. Particularly, the compounds provided by the present invention show in vivo antagonism against the excitation of the NMDA receptors under systemic administration and therefore, are especially useful for minimizing damage of the central nervous system induced by ischemic or hypoxic conditions such as stroke, hypoglycemia, cardiac arrest, and physical trauma, (see, J. McCulloch, Br. J. clin. Pharmacol., 34, 106 (1992)). The compounds are also useful in treatment of a number of neurodegenerative disorders including epilepsy, Huntington's chorea, Parkinson's disease, and Alzheimer's disease (reviews: G. Johnson, Annu. Rep. Med. Chem., 24, 41 (1989) and G. Johson and C. F. Bigge, ibid., 26, 11, (1991)). The present compounds also have analgetic, antidepressant, anxiolitic, and anti-schizophrenic activities, by virtue of this NMDA-glycine antagonism, as indicated by recent reports, e.g. A. H. Dickenson and E. Aydar, Neuroscience Lett., 121, 263 (1991), R. Trullas and P. Skolnick, Eur. J. Pharmacol., 185, 1 (1990), J. H. Kehne, et al., Eur. J. Pharmacol., 193, 283 (1991) P. H. Hutson, et al., Br. J. Pharmacol., 103, 2037 (1991 ), in which the reagents affecting glycine-binding site of NMDA receptors have shown such activities. Excessive release of glutamic acid and/or glycine from neuronal and glial cells results in overexcitation of NMDA receptor-$Ca^{2+}$ channel complexes and successive massive amount of $Ca^{2+}$ influx into the cell, which leads to neuronal cell death. NMDA-glycine antagonists described in the present invention would obviously regulate the amount of $Ca^{2+}$ influx from the glycine modulatory site of NMDA receptor-channel complex to maintain normal activities of neuronal cell. Therefore, the compounds of the present invention may be potential therapeutic agents for any diseases of animals including human caused by excessive glutamic acid and/or glycine release in addition to the diseases indicated above.

PRIOR ART

Certain indole-2-carboxylic acid derivatives are known to act as a antagonist of the glutamate receptors, especially the NMDA receptor subtype (J. Med. Chem., 33, 2944 (1990)). Unsubstituted tricyclic indole-2-carboxylic acid, 1,3,4,5-tetrahydrobenz[cd]indole-2-carboxylic acid has already been described in J. Am. Chem. Soc., 77, 3334 (1957). However, tricyclic indole-2-carboxylic acid derivatives having a substituent have not been reported.

DESCRIPTION OF INVENTION

The present invention provides a novel tricyclic indole-2-carboxylic acid derivative depicted by formula 1 or a pharmaceutically acceptable salt thereof:

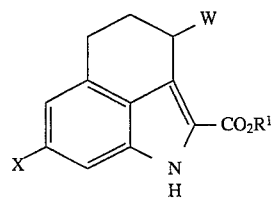

wherein

X represents an alkyl, halogen or cyano;

$R^1$ represents hydrogen, or a protecting group of carboxyl group;

W represents hydrogen, $—CO_2R^{3i}$, $—CONR^{3i}R^{4i}$, $—A—CO_2R^{3i}$ or $—A—CON R^{3i}R^{4i}$, wherein —A— represents an alkylene and $R^{3i}$ and $R^{4i}$ independently represent hydrogen, an alkyl, an aryl or a substituted aryl.

Among the $—A—CONR^{3i}R^{4i}$ group, a preferable $—NR^{3i}R^{4i}$ may be a group represented by formula 2,

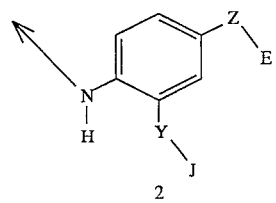

wherein $R^2$ represents hydrogen or a alkyl;

J represents an acidic group or a group which is convertible thereto in vivo;

E represents an basic group or a group which is convertible thereto in vivo;

Y represents a single bond, an alkylene, an alkenylene, a substituted alkylene or $Y—Q—Y^2$, wherein $Y^1$ represents a single bond or an alkylene, $Y^2$ represents an alkylene, and Q represents a heteroatom selected from oxygen or sulfur;

Z represents an alkylene.

The term "alkyl" as used herein includes straight chain or branched chain alkyl groups containing from 1 to 6 carbon atoms. Typical examples are methyl, ethyl, n-propyl, isopropyl, sec-butyl, tert-butyl, neopentyl, n-pentyl, and n-hexyl.

The term "halogen" as used herein includes fluorine, chlorine, bromine, and iodine. Typical example is chlorine.

The term "aryl" as used herein includes aryl groups containing from 6 to 10 carbon atoms. Typical examples are phenyl, 1-naphthyl, and 2-naphthyl.

The term "protecting group of carboxyl group" as used herein means the group which is readily hydrolyzed in vivo to give a hydrogen atom or the protecting group which is used for preventing undesired side reactions during the synthesis of the desired compounds. The group which is readily hydrolyzed in vivo to give a hydrogen atom includes alkyl and substituted alkyl, wherein alkyl is the same as mentioned above and the substituent of substituted alkyl includes straight chain or branched chain alkoxy groups containing from 1 to 6 carbon atoms such as methoxy, ethoxy, and tert-butoxy, straight chain or branched chain alkanoyloxy groups containing from 1 to 6 carbon atoms such as acetoxy, ethylcarbonyloxy, and pivaloyloxy, and aroyloxy group containing up to 11 carbon atoms such as benzoyloxy.

The protecting group which is used for preventing undesired side reactions during the synthesis includes substituted or unsubstituted benzyl such as benzyl, p-methoxybenzyl, and p-nitrobenzyl in addition to alkyl and substituted alkyl as mentioned above.

The term "alkylene" used in A includes straight chain or branched chain alkylene groups containing from 1 to 2 carbon atoms. Typical examples are methylene and methylmethylene. The most favorable example is methylene.

The substituent of substituted aryl includes alkyl, halogen, —Y—J, or —Z—E, wherein Y, J, Z, and E are as defined above. The number of the substituent(s) may be one or more which may be the same or different kinds.

The term "basic group" as used herein means the group which is readily protonated in vivo to provide cation. Typical examples are —$NH_2$, —$NHR^{3E}$, —$NR^{3E}R^{4E}$, —NH—C(=NH)—$NH_2$, —NH—C(=NH)—$NHR^{3E}$, and —NH—C(=NH)—$NR^{3E}R^{4E}$. Herein, $R^{3E}$ and $R^{4E}$ independently represent alkyl, cycloalkyl, alkenyl, or cycloalkylalkyl, or $R^{3E}$ and $R^{4E}$ are joined to form a cyclic amine together with the nitrogen atom.

The term "alkenyl" as used herein includes straight chain or branched chain alkenyl groups containing from 3 to 6 carbon atoms, of which an olefinic carbon atom may not be connected directly with the nitrogen atom of the basic group. Typical examples are allyl, 2-butenyl, and 3-butenyl.

The term "group which is convertible to a basic group in vivo" as used herein includes —NHL, —$NLR^{3E}$, —NH—C(=NL)—$NH_2$, —NH—C(=NL)—$NHR^{3E}$, and —NH—C(=NL)—$NR^{3E}R^{4E}$. Herein, L means a hydrolyzable group in vivo, such as alkanolyl group or alkoycarbonyl group, and $R^{3E}$ and $R^{4E}$ area as defined above.

The term "alkanoyl" as used herein includes straight chain or branched chain alkanoyl groups containing from 1 to 6 carbon atoms. Typical examples are formyl, acetyl, propanoyl, n-butanoyl, and pivaloyl.

The term "alkoxycarbonyl" as used herein includes straight chain or branched chain alkoxycarbonyl groups containing from 2 to 6 carbon atoms. Typical examples are methoxycarbonyl, ethoxycarbonyl, propoxycarbonyl, isopropoxycarbonyl, sec-butoxycarbonyl, and tert-butoxycarbonyl.

The term "acidic group" as used herein means the group which is readily deprotonated in vivo to provide anion. Typical examples are carboxyl and tetrazolyl.

The term "group which is convertible to an acidic group in vivo" as used herein means the group which generates the acidic group in vivo by hydrolysis. Typical examples are —$COOR^{3J}$, —$CONH_2$, —CON(OH)H, —$CONHR^{3J}$, —CON(OH)$R^{3J}$, —CON($OR^{5J}$)$R^{3J}$, or —$CONR^{3J}R^{4J}$, wherein $R^{3J}$ and $R^{4J}$ independently represent alkyl, cycloalkyl, alkenyl, or cycloalkylalkyl, or $R^{3J}$ and $R^{4J}$ are joined to form a cyclic amine together with the nitrogen atom, and $R^{5J}$ represents alkyl.

The term "cyclic amine" which $R^{3E}$ and $R^{4E}$, or $R^{3J}$ and $R^{4J}$ are joined to form includes 3 to 7 membered cyclic amine such as azetidine, pyrrolidine, or piperidine, and 5 to 7 membered cyclic amine containing other heteroatom such as oxygen or nitrogen atom as a ring member, such as piperazine, N-methylpiperazine, or morpholine.

The term "alkylene" as used in 2 includes straight chain or branched chain alkylene groups containing from 1 to 6 carbon atoms. Typical examples are methylene, dimethylene, trimethylene, tetramethylene, 2-methyltrimethylene, 3-methyltrimethylene, 1,1-dimethylmethylene, pentamethylene, and hexamethylene.

The term "alkenylene" as used herein includes straight chain or branched chain alkenylene groups containing from 2 to 6 carbon atoms. Typical examples are vinylene, 1-propenylene, 2-propenylene, 3-butenylene, 2-ethyl-3-butenylene, 4-pentenylene, 3-methyl-4-pentenylene, and 1-hexenylene.

The substituent of the term "substituted alkylene" for Y group includes hydroxy, —$OR^{3S}$, —$OCOR^{3S}$, amino, —$NHCOR^{3S}$, —$NHCO_2R^{3S}$, carboxyl, and $CO_2R^{3S}$, wherein $R^{3S}$ represents alkyl, cycloalkyl, alkenyl or cycloalkylalkyl. Typical examples of the "substituted alkylene" are —CH(OH)—, —CH(OAc)—, —CH($CO_2$-tert-Bu)—, and —$CH_2$—$CH_2$—CH($CO_2$Et)—. Preferably, the substituent and J group may be attached to the same carbon atom.

Typical examples of $Y^1$—Q—$Y^2$ are —O—$CH_2$—, —S—$CH_2$—, —$CH_2$—O— $CH_2$—, —$CH_2$—S—$CH_2$—, and —$CH_2CH_2$—O—CH($CH_3$)—.

The expression "pharmaceutically acceptable salt thereof" represents either a non-toxic acid addition salt or a non-toxic base salt.

The acid which forms non-toxic salt with the compounds provided by formula 1 includes inorganic acid such as hydrochloric, hydrobromic, sulfuric, and phosphoric acid or organic acid such as acetic, oxalic, citric, lactic, tartaric, malonic, fumaric, maleic acid, and methanesulfonic acid. On the other hand, the non-toxic base salt includes inorganic metal salts such as lithium, sodium, potassium, magnesium, aluminum, and barium salt or organic quaternary ammonium salt such as ammonium, triethylammonium, tetrabutylammonium, pyridinium, pyrrolidinium, or piperidinium salt.

When the compounds provided by the present invention have an asymmetric center, they exist as enantiomers. Such enantiomeric pure compounds and enantio-mixtures of these compounds are encompassed within the scope of the present invention. When the compounds of the invention have two or more asymmetric centers, they additionally exist as diastereomers. Such diastereomeric pure compounds and diastereo-mixtures of these compounds are also encompassed within the scope of the present invention.

The tricyclic indole-2-carboxylic acid derivatives of the present invention can be formulated to conventional pharmaceutical preparations such as tablets, pills, capsules, powders, granules, suspensions, or emulsions all for oral administration, and such as sterile parenteral solutions or suppositories for parenteral or rectal administration, respectively. The solid compositions such as tablets can be routinely prepared by mixing the active compound with conventional pharmaceutical carrier or diluent such as lactose, sucrose or corn starch, binder such as hydroxypropylcellulose, polyvinylpyrrolidone or hydroxypropylmethylcellulose, disintegrating agent such as sodium carboxymethylcellulose or sodium starch glycolate, lubricants such as stearic acid and magnesium stearate, or preservatives. For parenteral administration, the active compound is dissolved or suspended in a physiologically acceptable pharmaceutical carrier such as water, saline, oil or dextrose solution, which may contain auxiliary agent such as emulsifier, stabilizer, salt for influencing osmotic pressure or buffer, if desired. The dosage range can be varied widely depending on the severity of the particular disease, age, weight, and sex of the patient, and the route of administration. Typically, the effective dosage for oral administration is in the range of 1 to 1000 mg/day, preferably of 10 to 500 mg/day, for an adult patient, which may be given in a single dose or in multiple doses. For parenteral administration, the dosage range of 0.1 to 500 mg/day, more suitably of 3 to 100 mg/day for an adult patient can be employed with a single dose or with multiple doses.

Examples of compounds within the scope of the invention include:

7-Chloro-1,3,4,5-tetrahydrobenz[cd]indole-2-carboxylic acid;

Ethyl 7-chloro-1,3,4,5-tetrahydrobenz[cd]indole-2-carboxylate;

7-Chloro-3-carboxymethyl-1,3,4,5-tetrahydrobenz[cd]indole-2-carboxylic acid;

Methyl 7-chloro-3-t-butoxycarbonylmethyl-1,3,4,5-tetrahydrobenz[cd]-inodole-2 -carboxylate;

7-Chloro-3-phenylcarbamoylmethyl-1,3,4,5-tetrahydrobenz[cd]indole-2-carboxylic acid;

Methyl 7-chloro-3-phenylcarbamoylmethyl-1,3,4,5-tetrahydrobenz[cd]-indole-2 -carboxylate;

Methyl 7-chloro-3-(p-tert-butoxycarbonylaminomethyl-o-carboxyphenyl-carbamoylmethyl)-1,3,4,5 -tetrahydrobenz[cd]indole-2-carboxylate;

7-Chloro-3-(p-aminomethyl-o-carboxyphenylcarbamoylmethyl)-1,3,4,5-tetrahydrobenz[cd]indole-2 -carboxylic acid;

Methyl 7-chloro-3-[p-tert-butoxycarbonylaminomethyl-o-(methoxycarbonyl)phenylcarbamoylmethyl]-1,3,4,5 -tetrahydrobenz[cd]indole-2carboxylate;

Methyl 7-bromo-3-(p-tert-butoxycarbonylaminomethyl-o-carboxyphenyl-carbamoylmethyl)-1,3,4,5 -tetrahydrobenz[cd]indole-2-carboxylate;

7-Bromo-3-(p-aminomethyl-o-carboxyphenylcarbamoylmethyl)-1,3,4,5-tetrahydrobenz[cd]indole-2 -carboxylic acid;

Methyl 7-bromo-3-[p-tert-butoxycarbonylaminomethyl-o-(methoxycarbonyl)phenylcarbamoylmethyl]-1,3,4,5 -tetrahydrobenz[cd]indole-2carboxylate;

7-Bromo-3-[p-aminomethyl-o-(methoxycarbonyl)phenylcarbamoylmethyl]-1,3,4,5 -tetrahydrobenz[cd]indole-2-carboxylic acid;

Methyl 7-chloro-3-[p-tert-butoxycarbonylaminomethyl-o-(methoxycarbonylmethyl)phenylcarbamoylmethyl]-1,3,4,5 -tetrahydrobenz[cd]indole-2-carboxylate;

Methyl 7-chloro-3-[p-tert-butoxycarbonylaminomethyl-o-(carboxymethyl)phenylcarbamoylmethyl]-1,3,4,5 -tetrahydrobenz[cd]indole-2-carboxylate;

7-Chloro-3-[p-aminomethyl-o-(carboxymethyl)phenylcarbamoylmethyl]-1,3,4,5 -tetrahydrobenz[cd]indole-2-carboxylic acid;

Methyl 7-chloro-3-[p-tert-butoxycarbonylaminomethyl-o-(methoxycarbonylmethyl)phenylcarbamoylmethyl]-1,3,4,5 -tetrahydrobenz[cd]indole-2-carboxylate;

Methyl 7-chloro-3-[p-tert-butoxycarbonylaminomethyl-o-(carboxymethyl)phenylcarbamoylmethyl]-1,3,4,5 -tetrahydrobenz[cd]indole-2-carboxylate;

7-Chloro-3-[p-aminomethyl-o-(carboxymethyl)phenylcarbamoylmethyl]-1,3,4,5 -tetrahydrobenz[cd]indole-2-carboxylic acid;

Methyl 7-chloro-3-[p-(2,3-di-tert-butoxycarbonylguanidinomethyl)-o-(methoxycarbonylmethyl)phenylcarbamoylmethyl] -1,3,4,5-tetrahydrobenz[cd]-indole-2 -carboxylate;

Methyl 7-chloro-3-[p-(2,3-di-tert-butoxycarbonylguanidinomethyl)-o-(carboxymethyl)phenylcarbamoylmethyl]-1,3,4,5-tetrahydrobenz[cd]indole-2carboxylate;

7-Bromo-3-[p-guanidinomethyl-o-(carboxymethyl)phenylcarbamoylmethyl]-1,3,4,5 -tetrahydrobenz[cd]indole-2-carboxylic acid;

Methyl 7-bromo-3-[p-tert-butoxycarbonylaminomethyl-o-(2-methoxycarbonylethyl)phenylcarbamoylmethyl]-1,3,4,5 -tetrahydrobenz[cd]indole-2-carboxylate;

Methyl 7-bromo-3-[p-tert-butoxycarbonylaminomethyl-o-(2-carboxyethyl)phenylcarbamoylmethyl]-1,3,4,5 -1,3,4,5-tetrahydrobenz[cd]indole-2-carboxylate;

7-Chloro-3-[p-aminomethyl-o-(2-carboxyethyl)phenylcarbamoylmethyl]-1,3,4,5 -tetrahydrobenz[cd]indole-2-carboxylic acid;

Methyl 7-bromo-3-[p-tert-butoxycarbonylaminomethyl-o-(3-methoxycarbonylpropyl)phenylcarbamoylmethyl]-1,3,4,5 -tetrahydrobenz[cd]indole-2carboxylate;

Methyl 7-bromo-3-[p-tert-butoxycarbonylaminomethyl-o-(3-carboxypropyl)phenylcarbamoylmethyl]-1,3,4,5 -tetrahydrobenz[cd]indole-2carboxylate;

7-Bromo-3-[aminomethyl-o-(3-carboxypropyl)phenylcarbamoylmethyl]1,3,4,5 -tetrahydrobenz[cd]indole-2-carboxylic acid;

Methyl 7-chloro-3-[p-tert-butoxycarbonylaminomethyl-o-(tert-butoxycarbonylmethoxy)phenylcarbamoylmethyl]-1,3,4,5 -tetrahydrobenz[cd]indole-2carboxylate;

7-Chloro-3-[p-aminomethyl-o-(carboxymethoxy)phenylcarbamoylmethyl]-1,3,4,5 -tetrahydrobenz[cd]indole-2-carboxylic acid;

Methyl 7-chloro-3-[p-tert-butoxycarbonylaminomethyl-o-(ethoxycarbonylmethoxy)phenylcarbamoylmethyl]-1,3,4,5 -tetrahydrobenz[cd]indole-2carboxylate;

7-Chloro-3-[p-aminomethyl-o-(ethoxycarbonylmethoxy)phenylcarbamoylmethyl]-1,3,4,5 -tetrahydrobenz[cd]indole-2-carboxylic acid;

Methyl 7-chloro-3-[p-tert-butoxycarbonylaminomethyl-o-(tert-butoxycarbonylmethoxy)phenylcarbamoylmethyl]-1,3,4,5 -tetrahydrobenz[cd]indole-2carboxylate;

7-Chloro-3-[p-aminomethyl-o-(carboxymethoxy)phenylcarbamoylmethyl]-1,3,4,5 -tetrahydrobenz[cd]indole-2-carboxylic acid;

Methyl 7-chloro-3-[p-tert-butoxycarbonylaminomethyl-o-(4-ethoxycarbonylbutyl)phenylcarbamoylmethyl]-1,3,4,5 -tetrahydrobenz[cd]indole-2carboxylate;

Methyl 7-chloro-3-[p-tert-butoxycarbonylaminomethyl-o-(4-carboxybutyl)phenylcarbamoylmethyl]-1,3,4,5 -tetrahydrobenz[cd]indole-2-carboxylate;

7-Chloro-3-[p-aminomethyl-o-(4-carboxybutyl)phenylcarbamoylmethyl]1,3,4,5 -tetrahydrobenz[cd]indole-2-carboxylic acid;

7-Chloro-3-[aminomethyl-o-(3-carboxypropyl)phenylcarbamoylmethyl]-1,3,4,5 -tetrahydrobenz[cd]indole-2-carboxylic acid;

and salts thereof; wherein the numbering used for the tricyclic indole-2-carboxylic acid system is as shown in the following figure.

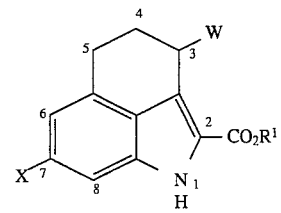

Process A-1

Compounds of formula 1a may be prepared according to the following scheme,

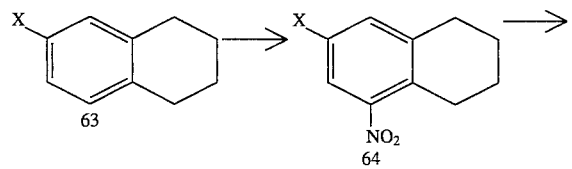

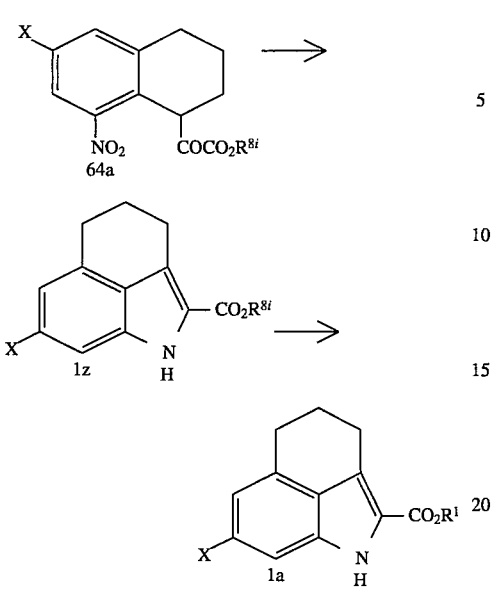

wherein X and $R^1$ are as defined above and $R^{8i}$ is alkyl, preferably methyl or ethyl.

1) Compounds of formula 63 wherein X is cyano, chloro, or bromo may be prepared by successively 1-1) nitration of tetralin, 1-2) reduction of the nitro tetralin to amino derivative, and 1-3) Sandmeyer or the modified Sandmeyer reaction. The nitration includes treatment with fuming nitric acid at 0° C. to ambient temperature, with nitric acid or isopropyl nitrate in concentrated sulfuric acid at 0° C. to ambient temperature, with a mixed reagent of trifluoroacetic anhydride and ammonium nitrate in a halogenated solvent such as chloroform or methylene chloride at ambient to refluxing temperature, or with nitronium tetrafluoroborate in a halogenated solvent such as chloroform or methylene chloride at ambient temperature. The reducing reagents including stannous dichloride, zinc, iron powder, and formate-palladium on carbon may be utilizable for reduction of the nitro tetralin. Sandmeyer and the modified Sandmeyer reaction are described in J. March, Advanced Organic Chemistry, p 601. First, the amino compound may be converted into diazonium compound by treatment with sodium nitrite at 0° C. in water. Treatment of the diazonium salt with CuCl, CuBr, or CuCN gives the corresponding compound of formula 63, wherein X is Cl, Br, or CN, respectively. Alternatively, treatment of the amino compound with an alkyl nitrite in the presence of $CuCl_2$, $CuBr_2$, or $CuCN_2$ in a halogenated solvent such as chloroform or dichloroethane at temperature range from 0° to 60° C. gives also the corresponding compound of formula 63, wherein X is Cl, Br, or CN, respectively.

Compound of formula 63 wherein X is iodo may be prepared by heating the compound of formula 63 wherein X is bromo with CuI in dimethyl sulfoxide at 150°~180° C.

Compound of formula 63 wherein X is fluoro may be prepared by reaction of tetralin with $XeF_2$ in dichloromethane at ambient temperature.

Compounds of formula 63 wherein X is alkyl may be prepared by reaction of compound of formula 63 wherein X is iodo or bromo with the corresponding Grignard reagent in the presence of a nickel catalyst such as $NiCl_2$ or nickel acetylacetonate in diethyl ether at −20° C. to ambient temperature.

2) Nitration of compounds of formula 63 may provide compounds of formula 64. Nitration conditions are as mentioned above.

3) Condensation of 64 with $(CO_2R^{8i})_2$ in the presence of a potassium alkoxide in an appropriate alcoholic solvent ($R^{8i}OH$) or an inert solvent such as diethyl ether at a temperature range from 0° to 60° C. may give 64a.

4) Reductive ring closure of compounds 64a to 1z may be effected by aqueous titanium trichloride in a protic solvent such as methanol, ethanol or acetic acid, or in an aprotic solvent such as acetone, THF or DMF at 0° C. to ambient temperature. Other reducing reagents including stannous dichloride, zinc, iron powder, and formate-palladium on carbon may be utilizable for the ring closure. Compounds of formula 1a wherein $R^1$ is hydrogen may be obtained by hydrolysis of compounds of formula 1z. The alkaline hydrolytic conditions include treatment with an alkaline metal hydroxide or carbonate such as lithium hydroxide, sodium hydroxide, potassium carbonate in a mixed solvent of water and a protic or aprotic solvent such as methanol, ethanol, or THF at temperature range of 0° to 50° C. The acidic hydrolytic conditions include treatment with an aqueous strong acid such as 1N~12N hydrochloric acid, or 5~48% hydrobromic acid in a protic or aprotic solvent such as acetic acid or dioxane at temperature range of ambient temperature to 100° C.

Compounds of formula 1a wherein $R^1$ is not hydrogen may be obtained by condensation of 1a ($R^1$=H) with $R^1OH$ ($R^1 \neq H$). The condensation may be carried out in the presence of a condensation reagent such as 1-ethyl-3-(3'-dimethylaminopropyl)carboximide-hydroxybenztriazole, isobutyric anhydride-triethylamine, and N,N-bis(2-oxo-3-oxazolidinyl)phosphinic chloride-triethylamine in an inert solvent such as DMF, THF, or dichloromethane at ambient temperature. Alternatively, compounds of formula 1a wherein $R^1$ is not hydrogen may be obtained by reaction of 1a ($R^1$=H) with $R^1T$ ($R^1 \neq H$) in the presence of a base such as sodium hydride and sodium hydroxide in an aprotic solvent such as THF, DMF, dimethyl sulfoxide, or hexamethylphosphonotriamide at ambient temperature, wherein T is a leaving group such as chloro, bromo, iodo, methanesulfonyloxy, toluenesulfonyloxy, and trifluoromethanesulfonyloxy.

Process A-2

Compounds of formula 1b and 1c may be prepared according to the following scheme;

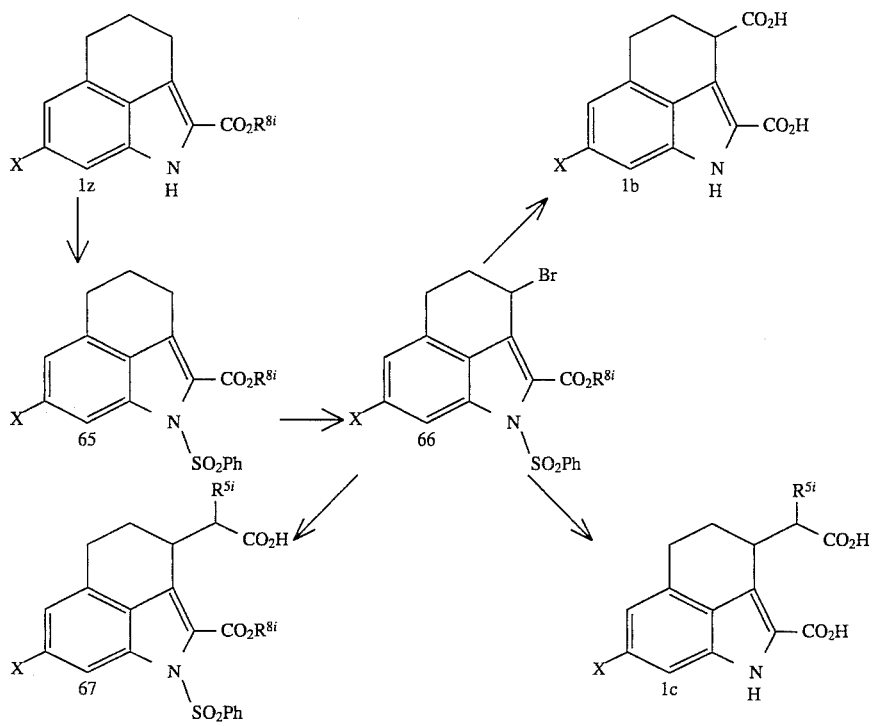

where X and $R^{8i}$ are as defined above and $R^{5i}$ is hydrogen or methyl.

1) Compounds of formula 1z may be protected with benzenesulfonyl chloride in an aprotic solvent such as THF or DMF in the presence of sodium hydride at ambient temperature to give 65.

2) Compounds 65 may be brominated with N-bromosuccinimide in the presence of azobisisobutyronitrile (AIBN) or benzoyl peroxide (BPO) in an inert solvent such as carbon tetrachloride or chlorobenzene under reflux to provide 66.

3) Treatment of 66 with potassium cyanide or sodium cyanide in an aprotic solvent such as DMF or dimethyl sulfoxide at temperature range of 50° to 80° C. followed by hydrolysis may provide 1b. The hydrolytic conditions are as mentioned above.

Treatment of 66 with a malonate $R^{5i}HC(CO_2R^{6i})_2$ in an aprotic solvent such as THF, DMF or dimethyl sulfoxide in the presence of a base such as sodium hydride at temperature range of 50° to 80° C. followed by hydrolysis may provide 1c, wherein $R^{6i}$ represents an alkyl, an aryl, or a substituted aryl. The hydrolytic conditions are as mentioned above. Under above conditions, use of $R^{5i}HC(CO_2\text{-}tBu)_2$ as a malonate followed by mild hydrolysis in refluxing toluene in the presence of a catalytic amount of p-toluenesulfonic acid and decarboxylation using hot acetic acid may provide mono carboxylic acid 67 which may be a useful intermediate for preparing compounds of the invention.

Various compounds of formulae 1d to 1k of the present invention may be prepared from the compounds of formula 1b or 1c according to the following schemes;

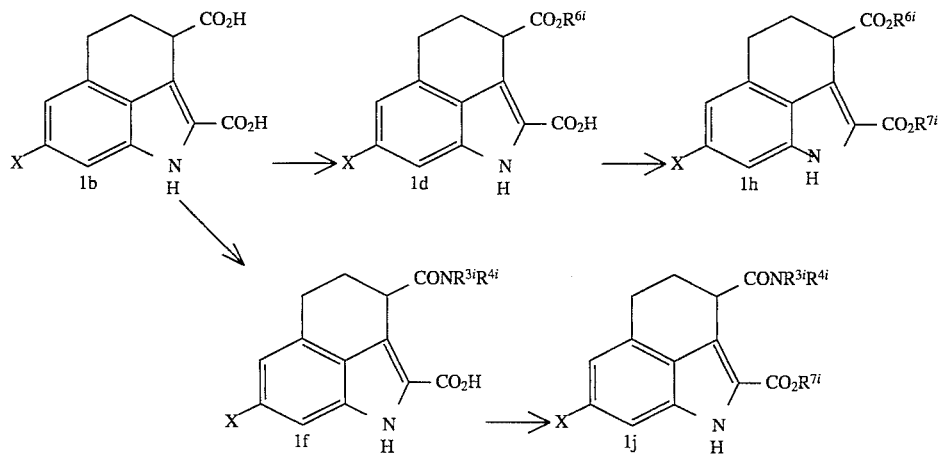

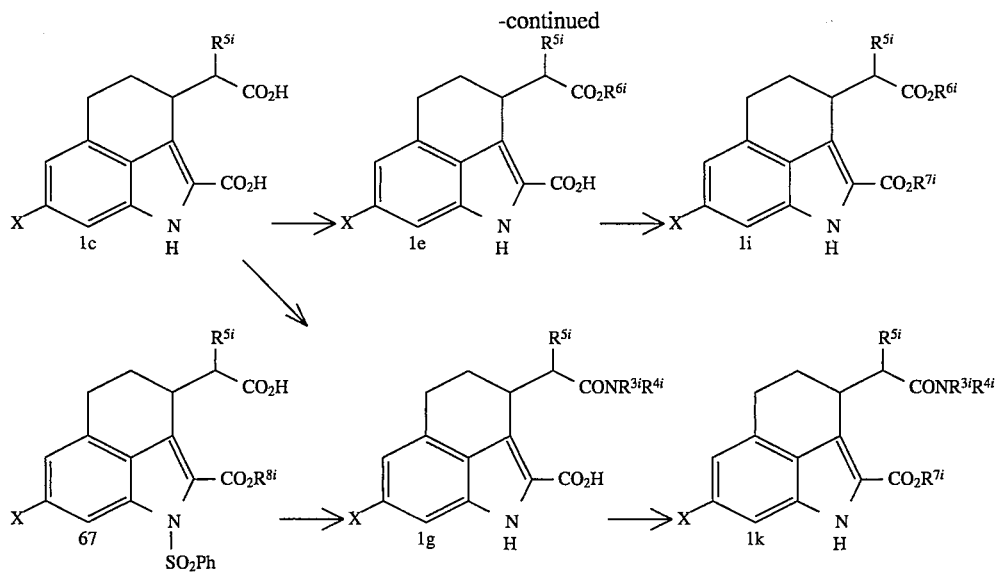

wherein, X, $R^{3i}$, $R^{4i}$, $R^{5i}$, and $R^{6i}$ are as defined above, and $R^{7i}$ represents a protecting group of carboxyl group.

Compounds of formula 1d or 1e may be prepared by condensation of 1b or 1c, respectively, with one equivalent of $R^{6i}OH$. The condensation conditions are as mentioned above.

Compounds of formula 1f or 1g may be prepared by condensation of 1b or 1c, respectively, with one equivalent of $R^{3i}R^{4i}NH$. The condensation conditions are as mentioned above. More conveniently, 1 g may be prepared by condensation of 67 with $R^{3i}R^{4i}NH$ followed by alkaline hydrolysis using an aqueous alkaline hydroxide such as sodium hydroxide or lithium hydroxide at ambient temperature in a protic or aprotic solvent such as methanol, ethanol, tetrahydrofuran (THF), or dimethoxyethane.

To synthesize compounds of formula 4 which correspond to compounds of formula 1g wherein $NR^{3i}R^{4i}$ is the group represented by 2, intermediate 6 is useful.

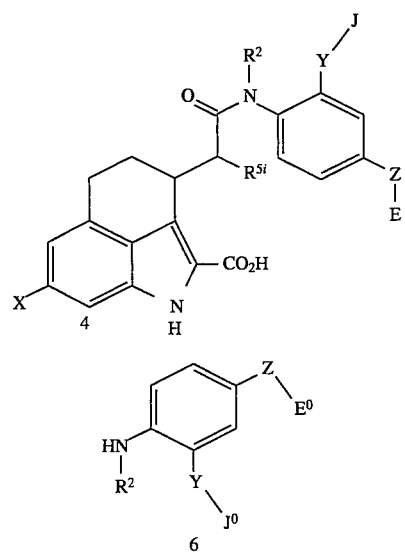

wherein X, Y, Z, J, E, $R^2$ and $R^{5i}$ are as defined above, $E^0$ represents —$NHL^1$ or —$NHC(=NL^1)NHL^1$, wherein $L^1$ represents a protecting group for basic group such as amino or guanidino group, preferably an alkoxycarbonyl such as t-butoxycarbonyl and $J^0$ represents a protected carboxyl group, preferably such as —$CO_2R^6$, wherein $R^6$ is an alkyl such as methyl, ethyl, or t-butyl.

Namely, Compounds of formula 4 wherein E is an basic group and J is $CO_2H$ may be prepared by condensation of 67 with 6 followed by alkaline hydrolysis using an aqueous alkaline hydroxide such as sodium hydroxide or lithium hydroxide at ambient temperature in a protic or aprotic solvent such as methanol, ethanol, tetrahydrofuran (THF), or dimethoxyethane and (if necessary) subsequent acidic hydrolysis including treatment with an aqueous strong acid such as 1N~12N hydrochloric acid, or 5~48% hydrobromic acid in a protic or aprotic solvent such as acetic acid or dioxane at temperature range of ambient temperature to 100° C.

Compounds of formula 4 wherein E is an basic group and J is $CO_2H$ may be re-protected to compounds of formula 4 wherein E is $E^0$ and J is $CO_2H$ by treatment with a dialkyl dicarbonate such as di-t-butyl dicarbonate in an inert solvent such as dichloromethane at ambient temperature.

Compounds of formula 4 wherein E is $E^0$ and J is $CO_2H$ may be condensed with $NH_3$, $NH_2R^{3J}$, $HNR^{3J}R^{4J}$, $HN(OH)R_{3J}$, $HN(OR^{5J})R^{3J}$, $H_2NOH$ or $HOR^{3J}$ to give compounds of formula 4 wherein J is $CONH_2$, $CONH R^{3J}$, $CONR3JR^{4J}$, $CON(OH)R^{3J}$, $CON(OR^{5J})R^{3J}$, $CON(OH)H$ or $CO_2R^{3J}$, respectively, wherein $R^{3J}$, $R^{4J}$ and $R^{5J}$ are as defined above and E is $E^0$. The condensation may be carried out in the presence of a condensation reagent such as 1-ethyl-3-(3'-dimethylaminopropyl)carboximide-hydroxybenztriazole, isobutyric anhydride-triethylamine, and N,N-bis(2-oxo-3-oxazolidinyl)phosphinic chloride-triethylamine in an inert solvent such as DMF, THF, or dichloromethane at 0° C. to ambient temperature.

Similar condensation of compounds of formula 4 wherein E is $E^0$ and J is $CO_2H$ with 3-aminopropionitrile followed by treatment of triphenyl-phosphine, diethyl azodicarboxylate, and trimethylsilyl cyanide in THF at ambient temperature and alkaline hydrolysis may provide compounds of formula 4 wherein J is tetrazolyl and E is $E^0$.

Compounds of formula 4 wherein E is $E^0$ may be selectively deprotected to compounds of formula 4 wherein E is —$NH_2$ or —$NHC(=NH)NH_2$ by mild acid hydrolysis. The hydrolytic conditions includes treatment with 0.1~4N hydrogen chloride in an inert solvent such as 1,4-dioxane or ethyl acetate at ambient temperature.

Compounds of formula 4 wherein E is —NHR$^{3E}$ or —NHC(=NH)NHR$^{3E}$ may be prepared by alkylation of compounds of formula 4 wherein E is —NH$_2$ or —NHC(=NH)NH$_2$ with R$^{3E}$I (R$^{3E}$ is as defined above) in the presence of a base such as potassium carbonate and sodium hydride. Compounds of formula 4 wherein E is —NR$^{3E}$R$^{4E}$ or —NHC(=NH)NR$^{3E}$R$^{4E}$ may also be prepared by further alkylation of compounds of formula 4 wherein E is —NHR$^{3E}$ or —NHC(=NH)NHR$^{3E}$ with R$^{4E}$I (R$^{3E}$ and R$^{4E}$ are as defined above) in the same manner as described above. Compounds of formula 4 wherein E is —NR$^{3E}$R$^{4E}$ or —NHC(=NH)NR$^{3E}$R$^{4E}$ wherein R$^{3E}$ and R$^{4E}$ are joined to form a cyclic amine may also be prepared by alkylation of compounds of formula 4 wherein E is —NH$_2$ or —NHC(=NH)NH$_2$ with 1-Q$^2$—1, wherein Q$^2$ represents an alkylene containing from 2 to 6 carbon atoms or an alkylene containing from 4 to 6 carbon atoms which is intervened with an oxygen or nitrogen atom, in the same manner as described above. Reductive amination using an appropriate aldehyde or ketone in the presence of sodium borohydride or sodium cyanoborohydride in an alcoholic solvent such as methanol at ambient temperature may also be utilized for introducing R$^{3E}$ and R$^{4E}$ groups.

Compounds of formula 4 wherein E is —NH$_2$, —NHR$^{3E}$, —NH—C(=NH)—NH$_2$, —NH—C(=NH)—NHR$^{3E}$, and —NH—C(=NH)—NR$^{3E}$R$^{4E}$ may be converted into compounds of formula 4 wherein E is —NHL, —NLR$^{3E}$, —NHC—C(=NL)—NH$_2$, —NH—C—(=NL)—NHR$^{3E}$, or —NH—C(=NL)—NR$^{3E}$R$^{4E}$, wherein L is R$^{17}$CO or R$^{17}$OCO wherein R$^{17}$ is alkyl, and R$^{3E}$ and R$^{4E}$ are as defined above. The conversion may be carried out by treatment with R$^{17}$COCl, (R$^{17}$CO)$_2$O, R$^{17}$OCOCl, or (R$^{17}$OCO)$_2$O in the presence of an organic base such as triethylamine or pyridine in an inert solvent such as dichloromethane at ambient temperature.

Compounds of formulae 1h, 1i, 1j, and 1k may be prepared by condensation of 1d, 1e, 1f, and 1g, respectively, with one equivalent of R$^{7i}$OH. The condensation conditions are as mentioned above.

Process A-3

Alternatively, modified compounds of formulae 1c and 1e, i.e. compounds of formulae 1m, 1n and 1p, may be prepared according to the following scheme;

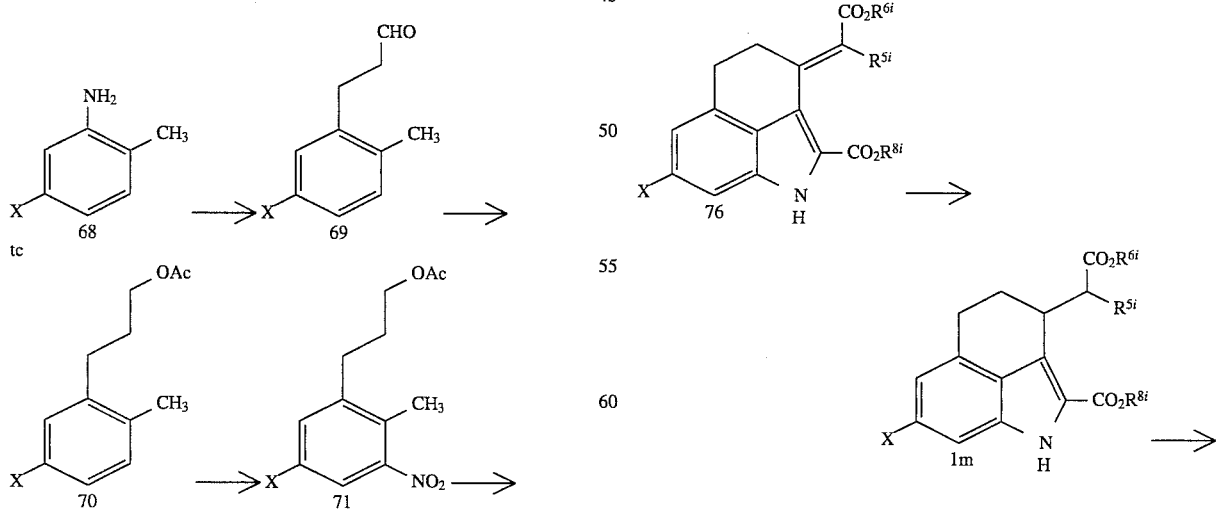

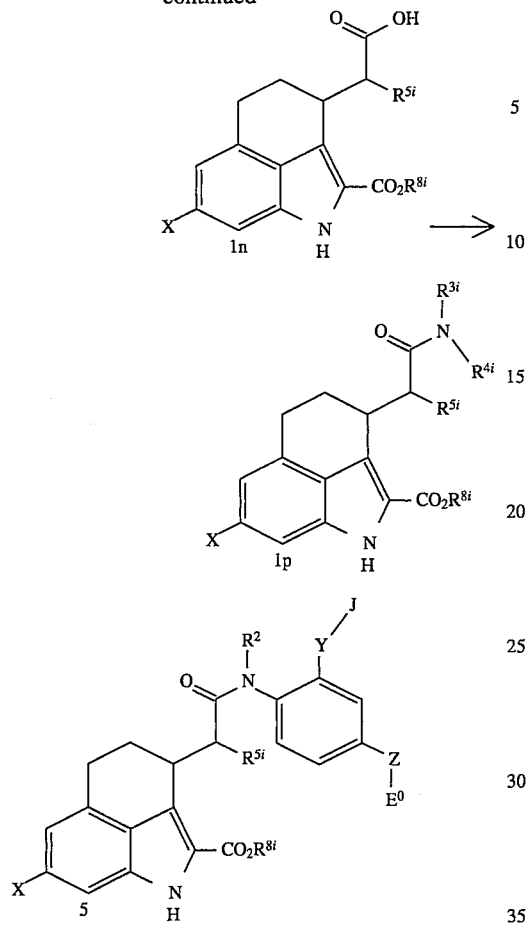

wherein X, $R^{5i}$, $R^{6i}$, $R^{8i}$, $R^2$, Y, $J^0$, Z and $E^0$ are as defined above.

1) First, compound 68 may be converted into the corresponding diazonium compound by treatment with sodium nitrite at 0° C. in water. Treatment of the diazonium compound with aqueous $TiCl_3$ in dimethylformamide (DMF)in the presence of acrolein gives 69, which may be converted into 70 by reduction with sodium borohydride in methanol at ambient temperature and acetylation with acetyl chloride-triethylamine in dichloromethane at 0° C. to ambient temperature.

2) Nitration of 70 with nitronium tetrafluoroborate in dichloromethane at ambient temperature may give 71.

3) Condensation of 71 with $(CO_2R^{8i})_2$ in the presence of a potassium alkoxide in an appropriate alcoholic solvent ($R^{8i}OH$) or an inert solvent such as diethyl ether at a temperature range from 0° to 60° C. may give 72.

4) Reductive ring closure of compounds 72 to 73 may be effected by aqueous titanium trichloride in a protic solvent such as methanol, ethanol or acetic acid, or in an aprotic solvent such as acetone, THF or DMF at 0° C. to ambient temperature.

5) Alcohol 73 may be oxidized with dimethyl sulfoxide-oxalyl chloride-triethyl amine in dichloromethane at −78° C. to give the corresponding aldehyde, which may be treated with $(EtO)_2POCHR^{5i}CO_2R^{6i}$ in the presence of a base such as sodium hydride or potassium t-butoxide in THF at −20° C. to ambient temperature or treated with a Wittig reagent $Ph_3P=CR^{5i}CO_2R^{6i}$ in toluene at reflux temperature of the solvent to give 74.

6) Bromination of 74 with N-bromosuccinimide in DMF at ambient temperature may provide 75.

7) Ring closure of 75 leading to 76 may be effected by intramolecular Heck reaction using a palladium catalyst such as $Pd(OAc)_2$ or $Pd_2(dba)_3 \cdot CHCl_3$ in the presence of triphenylphosphine in an inert solvent such as DMF, toluene, or acetonitrile at ambient temperature to 80° C.

8) Reduction of 76 with an appropriate reducing agent such as Wilkinson catalyst under hydrogen in an inert solvent such as methanol or toluene at ambient temperature to 80° C. or $NiCl_2$-sodium borohydride in methanol at ambient temperature may give compounds of formula 1m of the invention.

9) Hydrolysis of 1m may give 1c or 1e. The hydrolytic conditions are as mentioned above.

10) Compounds of formula 1m, wherein $R^{6i}$ is t-butyl and $R^{8i}$ is methyl or ethyl, may conveniently be converted into compounds of 1n of the invention by treatment with a catalytic amount of p-toluenesulfonic acid in refluxing toluene. Compounds of formula 1n may also be useful intermediates for making compounds of formula 1p including 5 of the invention.

Process A-4

The starting compounds 6 (6a and 6b) used in the above processes may be prepared as illustrated in the following scheme;

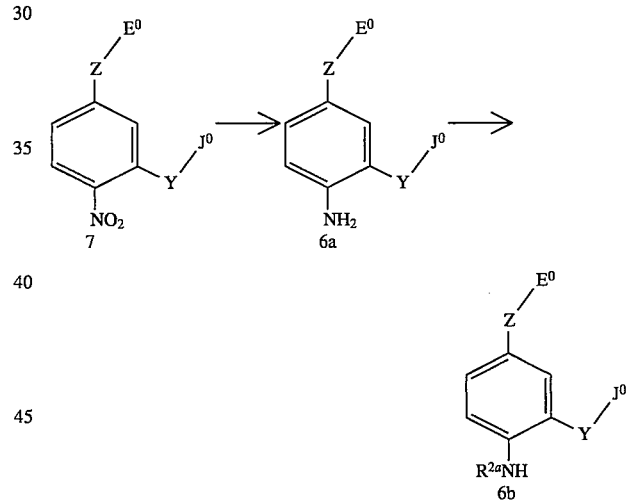

wherein Z, $E^0$, Y and $J^0$ are as defined above, and $R^{2a}$ is an alkyl.

Compounds 6a may be obtained by reduction of the corresponding nitrobenzene derivatives 7. The reduction may be performed with conventional catalytic hydrogenation on palladium/charcoal or palladium hydroxide in an inert solvent such as ethyl acetate, methanol, or ethanol. Compounds 6b may be prepared by alkylation of compounds 6a with $R^{2a}l$ in the presence of a base such as potassium carbonate or sodium hydride. Reductive amination using an appropriate aldehyde or ketone in the presence of sodium borohydride or sodium cyanoborohydride in an alcoholic solvent such as methanol at ambient temperature may also be utilized for the alkylation.

Process B

Compounds of formula 7a may be prepared starting from readily available 8;

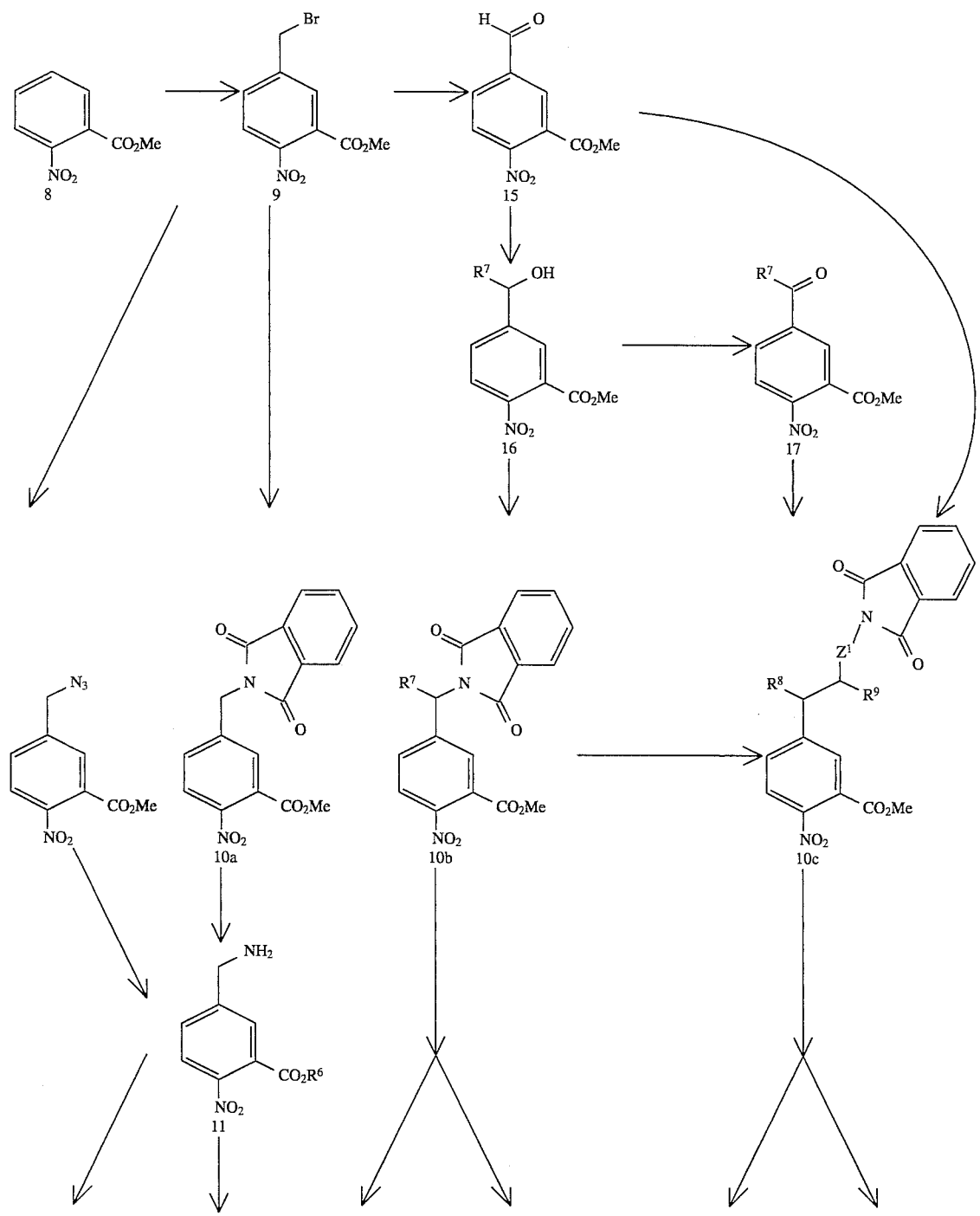

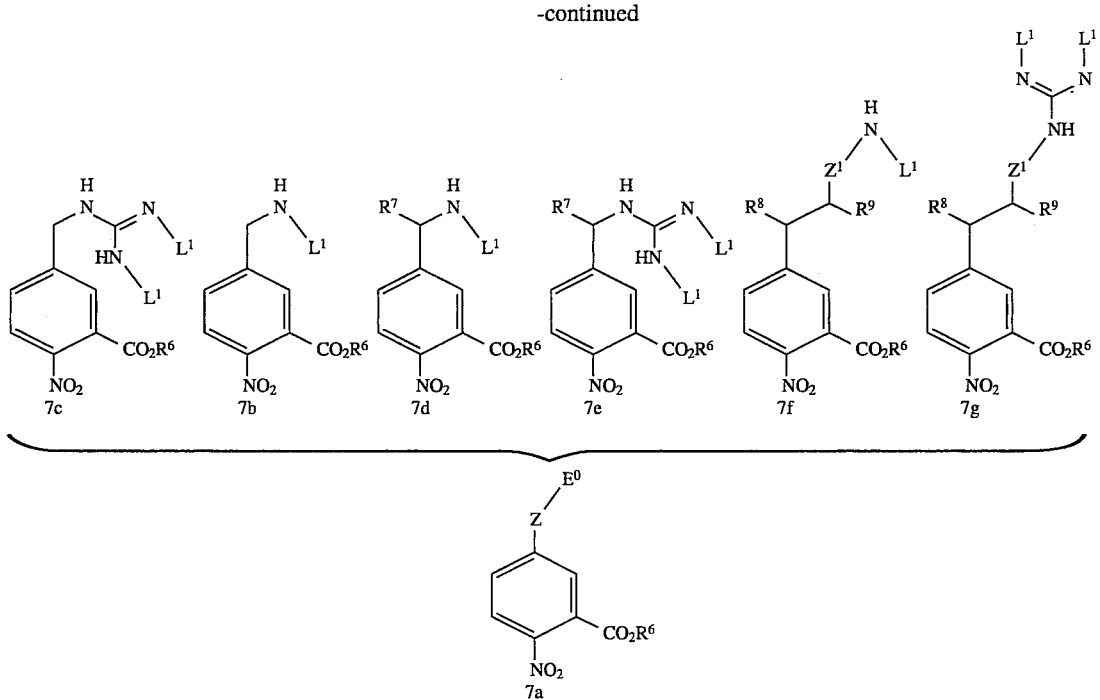

wherein Z, E⁰, L¹ and R⁶ are the same as defined above, R⁷ is alkyl, R⁸ is hydrogen or alkyl, R⁹ is hydrogen or alkyl, and Z¹ is a single bond or alkylene.

Process B-1

Compounds 8 may be converted into compounds of formula 7b and 7c, as outlined below.

1) Compounds 8 may be brominated with N-bromosuccinimide in the presence of azobisisobutyronitrile (AIBN) or benzoyl peroxide (BPO) in an inert solvent such as carbon tetrachloride or chlorobenzene under reflux to provide 9.

2) Treatment of 9 with potassium phthalimide in an aprotic solvent such as DMF at temperature range of 50° to 80° C. may provide 10a.

3) Hydrolysis of 10a under acidic conditions followed by reesterification with R⁶OH in the presence of an acid promoter such as thionyl chloride or hydrogen chloride may afford compounds 11. The hydrolytic conditions include treatment with an aqueous strong acid such as 6N~12N hydrochloric acid, or 25~48% hydrobromic acid in a protic or aprotic solvent such as acetic acid or dioxane at temperature range of 50° to 100° C. Hydrolysis of phthalimide group of 10a may be utilized by hydrazine or methylhydrazine in a protic solvent such as methanol at temperature range of 0° to 60° C. Compounds 11 may also be obtained by reaction of 9 with sodium azide in an aprotic solvent such as DMF at temperature range of 20° to 80° C. followed by hydrogenation over palladium/charcoal in an inert solvent such as ethyl acetate.

4) Free amines 11 may be protected with L¹ group to afford compounds of formula 7b. For example, reaction of 11 with di-t-butyldicarbonate in the presence of an organic base such as triethylamine in an inert solvent such as dichloromethane or ethyl acetate at ambient temperature affords compounds of formula 7b wherein L¹ is t-butoxycarbonyl. Treatment of 11 with MeSC(=NL¹)NHL¹ in the presence of an organic base such as triethylamine in an inert solvent such as dichloromethane or ethyl acetate at ambient temperature may afford compounds of formula 7c.

Process B-2

Compounds of formulae 7d and 7e may be prepared as outlined below.

1) Bromides 9 can be oxidized to aldehydes 15 by an appropriate oxidation conditions. The conditions include reaction with dimethyl sulfoxide and trimethylamine N-oxide in dichloromethane at temperature range of 20° to 40° C.

2) Treatment of 15 with an alkylating reagent such as R⁷MgBr or R⁷Li in diethyl ether or THF at temperature range of −20° to 0° C. provides alcohols 16.

3) Mitsunobu reaction of 16 by using phthalimide, triphenylphosphine, and diethyl azodicarboxylate in THF at ambient temperature may afford compounds 10b, which may be converted into compounds of formula 7d and 7e, as described in the conversion of 10a into the compounds of formula 15 7b and 7c.

Process B-3

Compounds of formula 7f and 7g, may be prepared as outlined below.

1) Alcohols 16 may be oxidized to the corresponding ketones 17 by an appropriate oxidation conditions. The conditions include treatment with manganese oxide in dichloromethane at room temperature, treatment with DMSO-ClCOCOCl-triethylamine in dichloromethane at −70° C., treatment with pyridinium chlorocromate in dichloromethane at ambient temperature, and treatment with Dess-Martin reagent.

2) Reaction of aldehydes 15 or ketones 17 with Wittig reagent $PPh_3=CR^9-Z^1$-phthalimide in an inert solvent such as THF at temperature range of −70° to 60° C. followed by reduction with diimine generated from reaction of potassium azodicarboxylate with acetic acid in acetonitrile at temperature range of −20° to 0° C.

Process C-1 and C-2

Compounds of formula 7h and 7i may be prepared as illustrated in the following scheme;

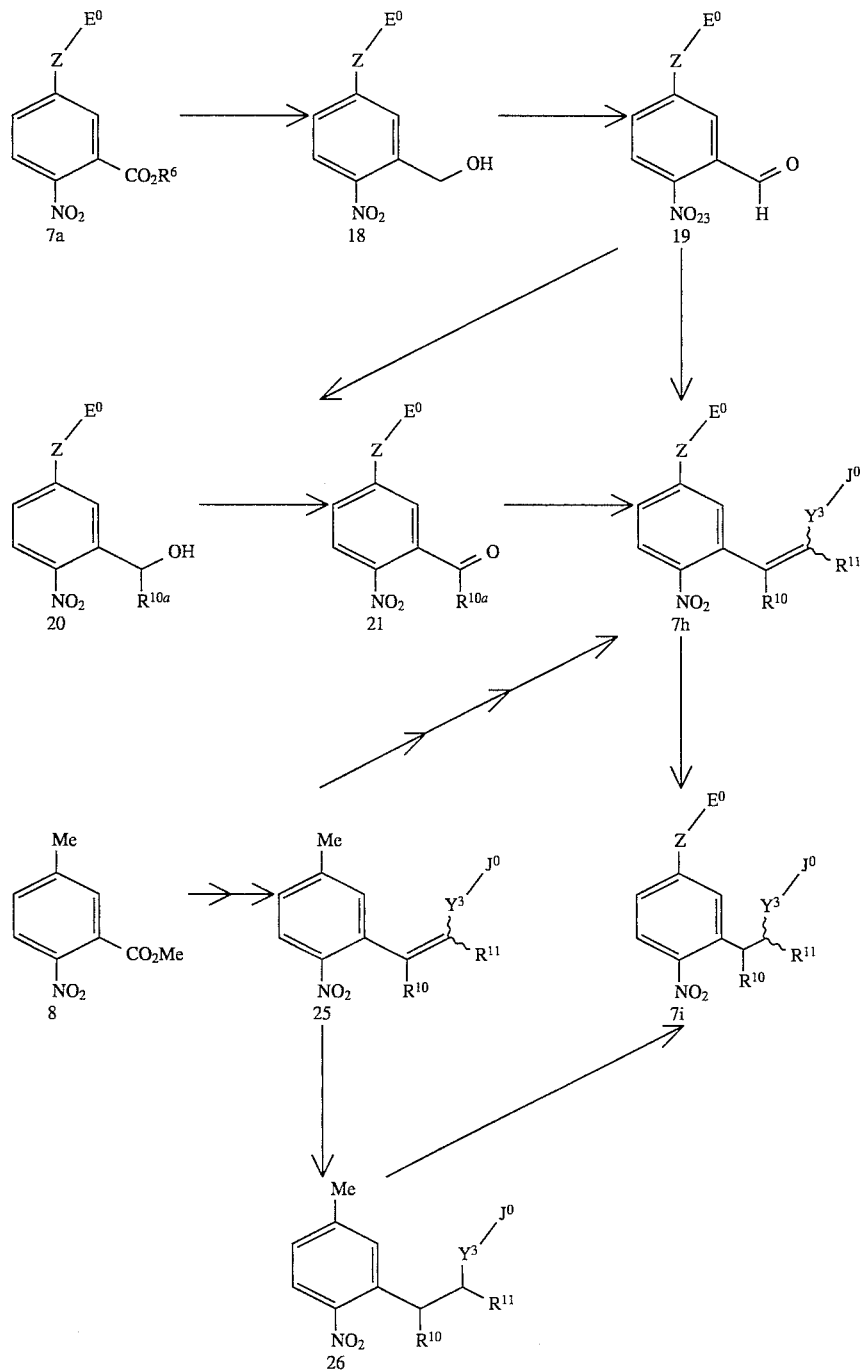

affords compounds 10c, which may be converted into compounds of formula 7f and 7g as described in the conversion 10a into the compounds of formula 7b and 7c.

wherein $R^{10}$ and $R^{11}$ are independently hydrogen or alkyl, $Y^3$ is a single bond or an alkylene, $R^{10a}$ is an alkyl, and Z, $E^0$ and $J^0$ are as defined above.

Process C-1

1) Compounds 7a may be reduced to alcohols 18 by using sodium borohydride-methanol in THF at ambient to refluxing temperature.
2) Alcohols 18 may be oxidized to the corresponding aldehydes 19 under the conditions described in the conversion of 16 to 17.
3) Treatment of 19 with an alkylating reagent such as $R^{10a}MgBr$ or $R^{10a}Li$ in diethyl ether or THF at temperature range of $-20°$ to $0°$ C. provides alcohols 20.
4) Alcohols 20 may be oxidized to the corresponding ketones 21 by an appropriate oxidation condition. The conditions include treatment with DMSO-ClCOCOCl-triethylamine in dichloromethane at $-70°$ C., treatment with pyridinium chlorocromate in dichloromethane at ambient temperature, and treatment with Dess-Martin reagent.
5) Reaction of aldehydes 19 or ketones 21 with a Wittig reagent $PPh_3=CR^{11}-Y^3-J^0$ in an inert solvent such as THF at temperature range of $-70°$ to $60°$ C. affords compounds of formula 7h, which may be selectively reduced to compounds of formula 7i, by catalytic hydrogenation using palladium/charcoal or by diimine reduction.

Process C-2

Alternatively, compounds of formula 7h and 7i may be prepared starting from compounds 8 as described below.

1) Compounds 8 may be converted into compounds 25 and 26 according to a sequence analogous to that used in the conversion of compounds 7a into compounds 7h and 7i, respectively (process C-1).
2) Compounds 25 and 26 may be converted into the corresponding compounds 7h and 7i, respectively, according to a sequence analogous to that used in the conversion of 8 into compounds 7a (process B).

Process C-3

Convenient methods for making a $-Y-J^0$ part of formula 7 may be a use of malonate anion.

Compounds of formula 32 and 7j may be prepared as illustrated in the following scheme;

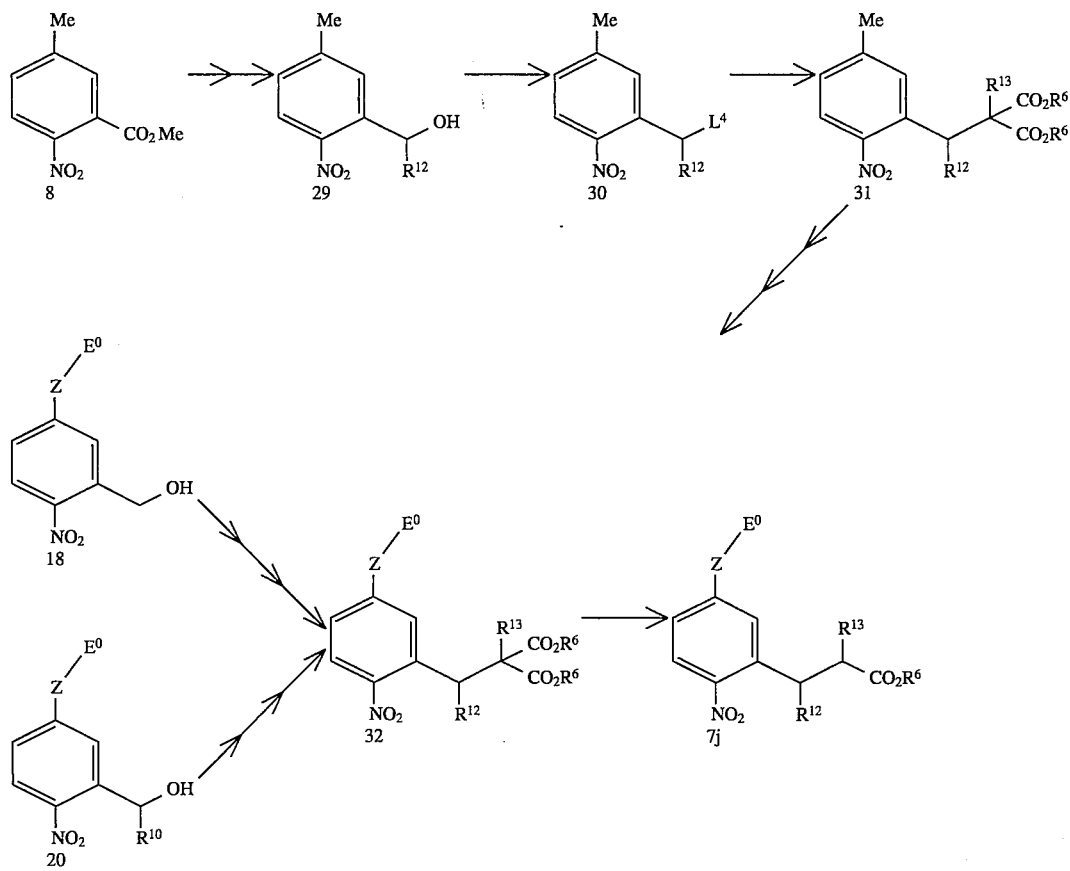

wherein Z, $E^0$, $R^6$ and $R^{10}$ are as defined above, $R^{12}$ is hydrogen or an alkyl, $R^{13}$ is hydrogen or an alkyl, and $L^4$ is a leaving group such as Cl, Br, I, $OSO_2Ph$, or $OSO_2CF_3$.

Compounds 8 may be converted into alcohols 29 by a sequence analogous to that used in the conversion of compounds 7a into 18 and 20 (process C-1, 1)~3)). Compounds 29 may be converted to 30. Herein, Cl and Br may be introduced by reaction with $SOCl_2$ or $SOBr_2$, and $CCl_4$—$PPh_3$ or $CBr_4$—$PPh_3$, respectively and I may be introduced by reaction of $I_2$—$PPh_3$-imidazole in an inert solvent at temperature range of $0°$ to $50°$ C. $PhSO_2O$— and $CF_3SO_2O$— groups may be prepared by reaction with $PhSO_2Cl$-triethylamine and $(CF_3SO_2)_2O$-triethylamine, respectively in an inert solvent such as dichloromethane at $0°$ C. to ambient temperature. Treatment of 30 with $R^6OCOCHR^{13}CO_2R^6$ in the presence of a base such as sodium hydride, potassium t-butoxide, and lithium hexamethyldisilazide in an aprotic solvent such as THF, DMF, or DMSO at temperature range of 0° to 60° C. provide 31. Compounds 31 may be converted into compounds 32, which are inclusive in compounds of formula 7, according to a sequence analogous to that used in the conversion of 8 into compounds of formula 7a (process B). In some cases, an alkoxycarbonyl group of 32 may be simultaneously decarboxylated during the hydrolysis step of the phthalimide group to afford compounds of formula 7j. Alternatively, 18 and 20 may be converted into compounds 32 by a sequence similar to that described in the conversion of 29 to 31.

Process C-4

Compounds of formula 36 and 7k, may be prepared as illustrated in the following scheme;

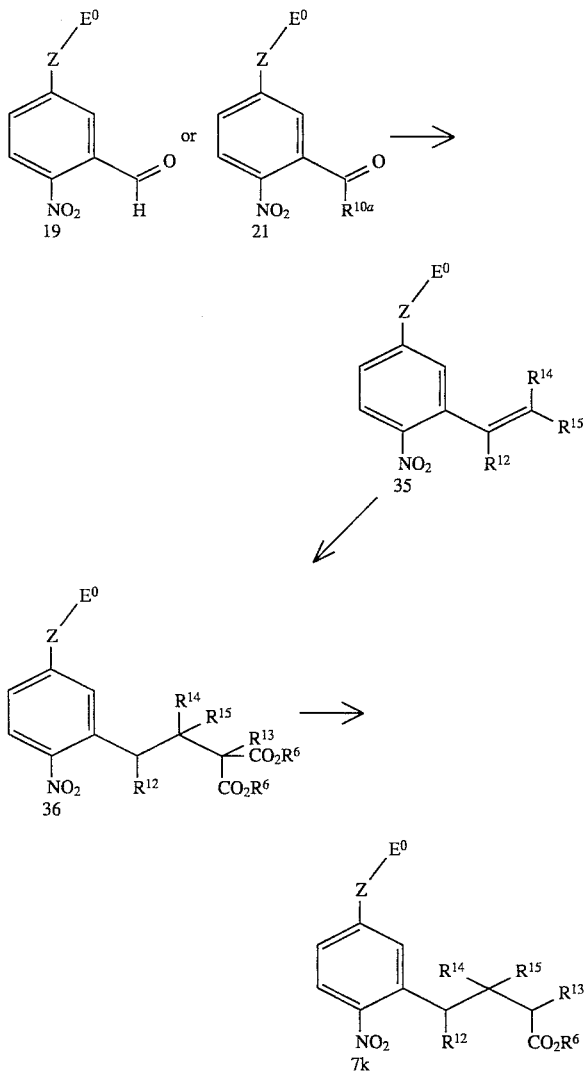

wherein Z, $E^0$, $R^6$, $R^{10a}$, $R^{12}$ and $R^{13}$ are as defined above, $R^{14}$ and $R^{15}$ are independently hydrogen or an alkyl.

Compounds 19 and 21 may be converted into 35 by Wittig reaction with $PPh_3=CR^{14}R^{15}$ in an inert solvent such as THF at temperature range of —70° to 60° C. Reaction of 35 with anion of $R^6OCOCHR^{13}CO_2R^6$ under conditions similar to those mentioned in the conversion of 30 into 31 may provide compounds 36 which are inclusive in compounds of formula 7. An alkoxycarbonyl group of compounds 36 may be decarboxylated to hydrogen, if necessary, to provide compounds of formula 7k, under certain conditions such as heating in DMSO at elevated temperature in the presence of a salt such as sodium chloride.

Process C-5

Compounds of formula 7m and 7n, may be prepared as illustrated in the following scheme;

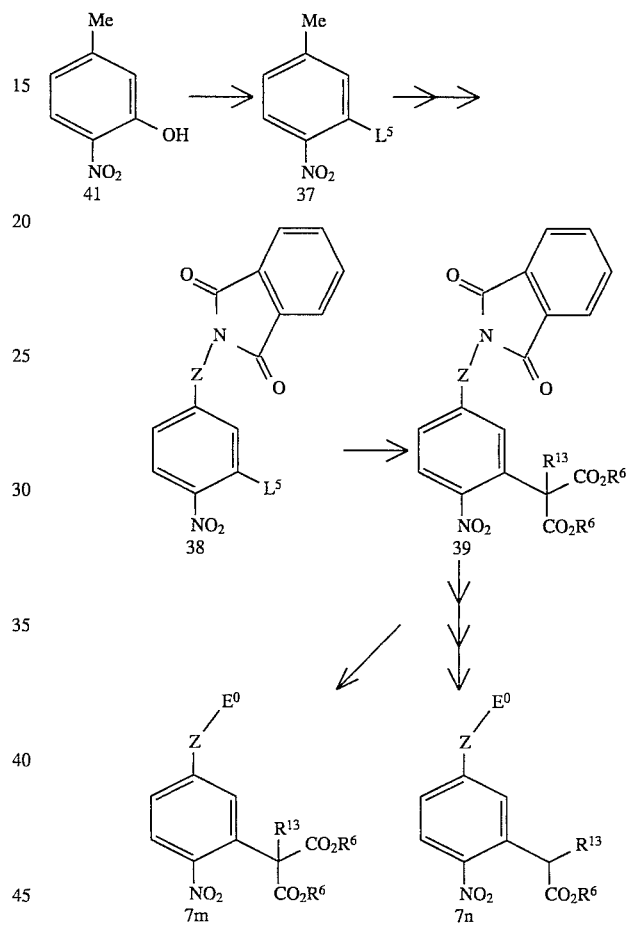

wherein Z, $E^0$, $R^6$ and $R^{13}$ are as defined above, and $L^5$ is a leaving group such as $OSO_2Ph$ or $OSO_2CF_3$.

Compounds 37 readily prepared from 41 as described in the conversion of 29 to 30 (process C-3), may be converted into 38 by a method similar to that described in the conversion of 8 into 10a,b,c (process B). Reaction of 38 with an anion of $R^6OCOCHR^{13}CO_2R^6$ as mentioned in synthesis of 31 (process (3-3) may provide compounds 39 which may be converted into compounds of formula 7m and 7n, according to a sequence analogous to that used in the conversion of 10a,b,c into the corresponding compounds of formula 7a (process B).

Process D-1

Compounds of formula 7p, may be prepared as illustrated in the following scheme;

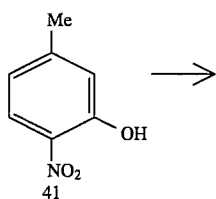

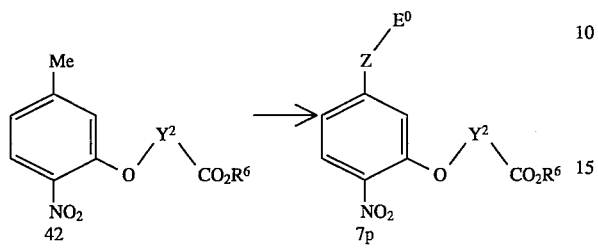

wherein $Y^2$ is an alkylene, and Z, $E^0$ and $R^6$ are as defined above.

Compounds of formula 7p may be prepared from compound 41. Reaction of 41 with $BrY^2CO_2R^6$ in the presence of a base such as potassium carbonate, potassium t-butoxide, or sodium hydride in an inert solvent such as acetonitrile, THF, DMF, or DMSO at temperature range of 0° to 60° C. may provide compounds 42. Conversion of 42 into compounds of formula 7p may be performed as described in the conversion of 8 into compounds of formula 7a (process B).

Process D-2

Compounds of formula 7q, may be prepared as illustrated in the following scheme;

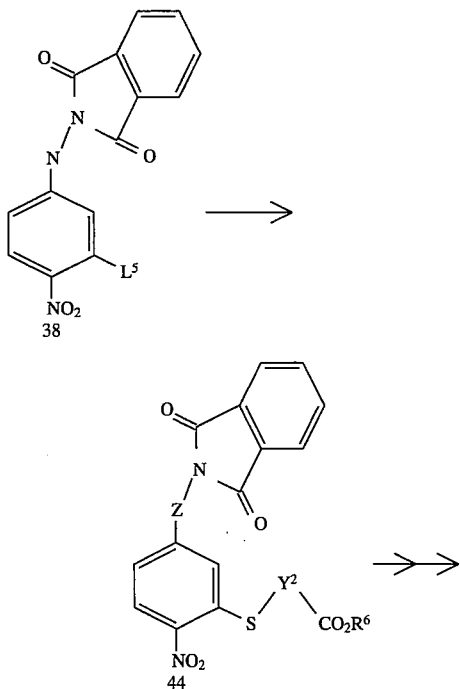

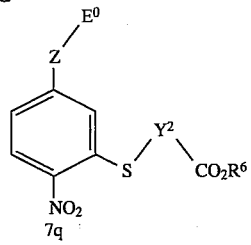

wherein Z, $E^0$, $Y^2$, $L^5$ and $R^6$ are as defined above.

Compounds of formula 7q may be prepared from compounds 38. Reaction of 38 with $HS-Y^2CO_2R^6$ in the presence of a base such as sodium hydride, potassium t-butoxide, and lithium hexamethyldisilazide in an aprotic solvent such as THF, DMF, or DMSO at temperature range of 0° to 60° C. may provide 44. Conversion of 44 into compounds of formula 7q may be performed as described in the conversion of 10a,b,c into the corresponding compounds of formula 7a (process B).

Process E-1

Compounds of formula 7r, may be prepared as illustrated in the 5 following scheme;

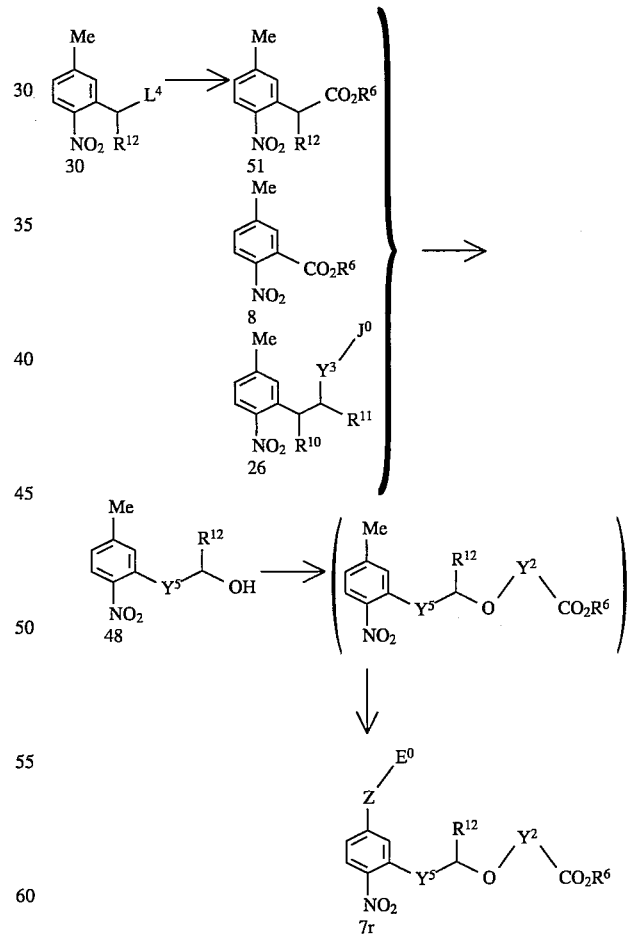

wherein Z, $E^0$, $J^0$, $L^4$, $Y^3$, $Y^2$, $R^{12}$ and $R^6$ are as defined above, and $Y^5$ is a single bond or an alkylene.

Reaction of 30 with sodium cyanide in an aprotic solvent such as THF, DMF, or DMSO at ambient temperature to 60°

C. followed by acid hydrolysis and esterification may provide compounds 51. Compounds 8, 26, and 51 may readily be converted into compounds of formula 48 as described in the conversion of 8 into 29 (process C-3). Reaction of 48 with $BrY^2CO_2R^6$ as described in the conversion of 41 to 42 (Process D-1) followed by an transformation similar to that described in the conversion of 8 into compounds of formula 7a (process B) may provide compounds of formula 7r.

Process E-2

Compounds of formula 7s, may be prepared as illustrated in the following scheme;

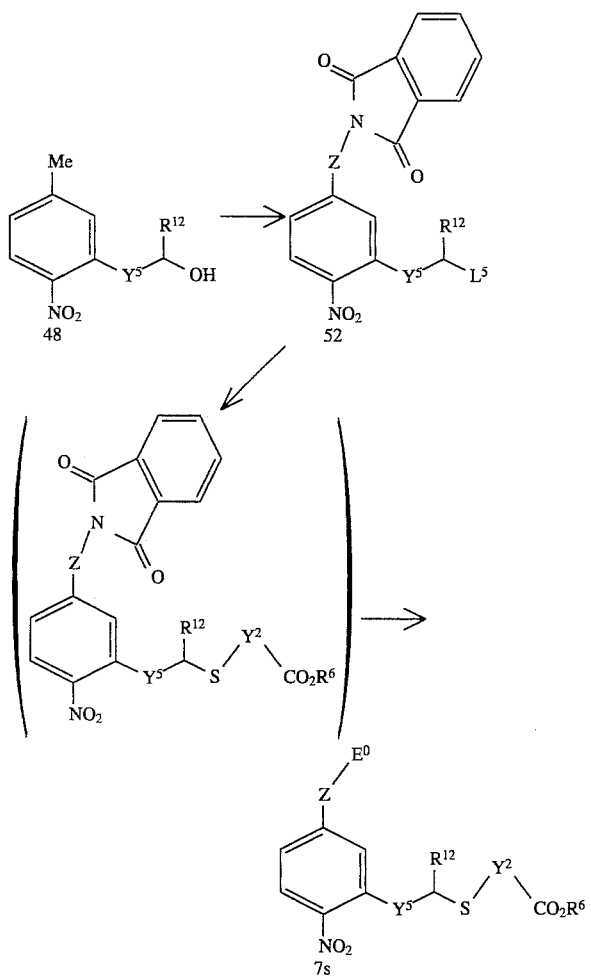

wherein Z, $E^0$, $L^5$, $Y^5$, $Y^2$, $R^{12}$ and $R^6$ are as defined above.

Compounds 48 may be converted into compounds 52, as described in the conversion of 41 to 38 (process C-5). Reaction of 52 with $HSY^2CO_2R^6$ as described in the conversion of 38 to 44 (process D-2) followed by transformation similar to that described in the conversion of 10a,b,c into the corresponding compounds of formula 7a (process B) may provide compounds of formula 7s.

Process F-1

Compounds of formula 7t, may be prepared as illustrated in the following scheme;

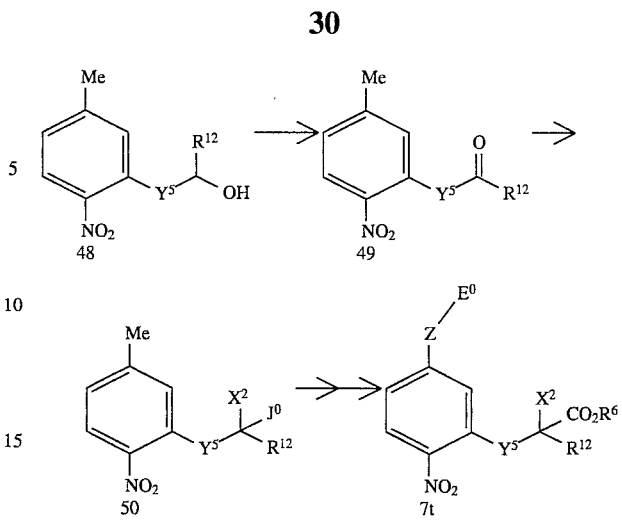

wherein Z, $E^0$, $J^0R^{,R6}$, $Y^5$ and $R^{12}$ are as defined above, and $X^2$ is $R^{3S}O-$, $R^{3S}CO_2-$, $R^{3S}CONH-$, or $R^{S3}OCONH-$.

Compounds 48 may readily be oxidized into compounds of formula 49, as described in the conversion of 16 to 17 (process B). Treatment of 49 with trimethylsilyl cyanide in the presence of zinc iodide in dichloromethane at temperature range of 0° to 40° C. followed by acid hydrolysis and, successive protection of the resulting carboxylic acid into $J^0$ and the alcohol into $X^2$ may provide compounds of formula 50 wherein $X^2$ represents $R^{3S}O-$ or $R^{3S}COO-$ wherein $R^{3S}$ is as defined above. The protection of the alcohol to— $OR^{3S}$ may be carried out by treatment with $R^{3S}I$ in the presence of a base such as sodium hydride, potassium carbonate, and lithium hexamethyldisilazide in an aprotic solvent such as DMF, THF, or DMSO at temperature range of 40° to 80° C. The protection of the alcohols to $—OCOR^{3S}$ may be carried out by treatment with $R^{3S}COCl$ or $(R^{3S}CO)_2O$ in the presence of an organic base such as triethylamine and pyridine in an inert solvent such as dichloromethane at ambient temperature.

Similarly, compounds 49 may be converted into compounds of formula 50 wherein $X^2$ represents $R^{3S}CONH-$ and $R^{3S}OCONH-$ by conventional Strecker or Bucherer synthesis followed by protection. The protection of the resulting amine may be carried out by treatment with $R^{3S}COCl$, $(R^{3S}CO)_2O$, $R^{3S}OCOCl$, or $(R^{3S}OCO)_2O$ in the presence of an organic base such as triethylamine or pyridine in an inert solvent such as dichloromethane at ambient temperature.

Compounds 50 may be transformed into compounds of formula 7t, by a route similar to that described in the conversion of 8 into compounds 7a (process B).

Process F-2

Compounds of formula 7u, may be prepared as illustrated in the following scheme;

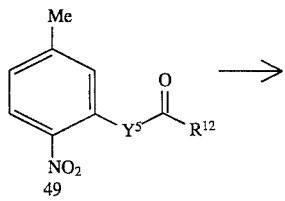

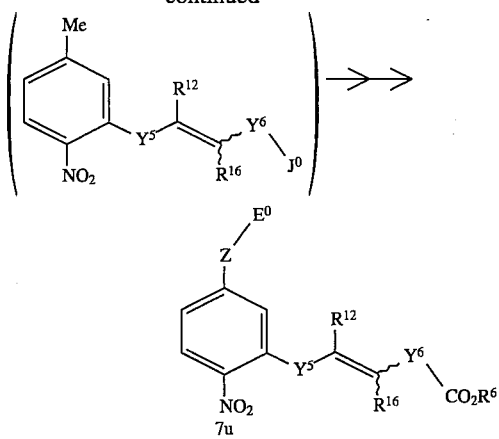

wherein Z, E⁰, J⁰, Y⁵, R¹² and R⁶ are as defined above, Y⁶ is a single bond or an alkylene, R¹⁶ is hydrogen or an alkyl.

Reaction of compounds of formula 49 with a Wittig reagent $PPh_3=CR^{16}-Y^6-J^0$ in an inert solvent such as THF at temperature range of −70° to 60° C. followed by transformation similar to that described in the conversion of 8 into compounds 7a (process B) affords compounds of formula 7u.

According to the methods as described above, the compounds of the invention may be prepared as racemic form. However, the compounds of the invention may be obtained as enantiomeric pure form by resolving an appropriate racemic intermediate during the synthesis, or the compounds of the invention themselves. The resolution includes salt-formation of the compound having a basic moiety with optically pure acid such as (+)-tartaric acid, and also salt-formation of the compound having an acidic moiety with optically pure amine such as quinine or quinidine, followed by fractional recrystallization and regeneration of the parent compound. The resolution technique also includes amide or ester formation of the compound having carboxylate, amine, or alcohol with chiral-auxiliary, followed by chromatographic separation and removal of the auxiliary. Alternative resolution technique includes enzymatic hydrolysis of the ester or amide of the intermediate during the synthesis or the compound of the invention.

A certain compound of the invention may be obtained by using conventional protection-deprotection techniques, if necessary or desirable, during synthesis as described above. Such techniques are described in T. W. Greene, Protective Groups in Organic Synthesis, John Wiley & Sons, 1981.

The compounds of the present invention strongly inhibit both [³H] 5,7-dichlorokynurenic acid (DCKA) and [³H] glycine binding to the rat brain synaptic membrane preparation, implying that these compounds possess the potent affinities for strychnine-insensitive glycine modulatory site of NMDA (N-methyl D-aspartate) receptors (see, for example, Y. Yoneda, et al., J. Neurochem., 60, 634 (1993)). The activities of the compounds were measured by [³H] DCKA and [³H] glycine binding inhibition studies as illustrated below. [³H] glycine binding studies A crude rat brain synaptic membrane preparation was washed three times by centrifugation at 50,000×g for 30 min with 50 mM tris acetate (pH 7.4). The pellets obtained were suspended in 0.23M sucrose solution and stored at −80° C. For binding studies, the frozen suspension was thawed, treated with 0.08% triton X-100 at 2° C. for 10 min, and washed twice by the centrifugation as mentioned above. The synaptic membrane thus prepared (ca. 150~200 µg of protein) was incubated with 10 nM [³H] glycine (1.11 TBq/mmol) and the test compound (10 ng/mL~0.1 ng/mL) at 2° C. for 10 min in 50 mM tris acetate (pH 7.4). The incubation was terminated by suction filtration using Whatman GF/B glass filter. The radioactivity bound to the membrane on the filter was measured by scintillation counting. Non-specific binding was calculated by the radioactivity measured under the incubations in the presence of 0.1 mM D-serine. The [3H] glycine binding was not inhibited by addition of 0.1 mM strychnine. Compound of Example 5 (10 ng/mL) showed 69% inhibition of the [³H] glycine binding.

[³H] DCKA binding studies

A crude rat brain synaptic membrane preparation was washed three times by centrifugation at 50,000×g for 30 min with 50 mM tris acetate (pH 7.4). The pellets obtained were suspended in 0.23M sucrose solution and stored at −80° C. For binding studies, the frozen suspension was thawed, treated with 0.08% triton X-100 at 2° C. for 10 min, and washed twice by the centrifugation as mentioned above. The synaptic membrane thus prepared (ca. 100 µg of protein) was incubated with 10 nM [³H] (DCKA) (603 GBq/mmol) and the test compound (10 ng/mL~0.1 ng/mL) at 2° C. for 10 min in 50 mM tris acetate (pH 7.4). The incubation was terminated by suction filtration using Whatman GF/B glass filter. The radioactivity bound to the membrane on the filter was measured by scintillation counting. Non-specific binding was calculated by the radioactivity measured under the incubations in the presence of 0.1 mM glycine. Compound of Example 5 (10 ng/mL) showed 94% inhibition of the [³H] DCKA binding.

The compounds of the present invention attenuated strongly NMDA-induced seizure under systemic administration in the following in vivo model.

NMDA-induced seizure model

Thirty min later following intraperitoneal administration of the test compound (0.3~30 mg/kg) into each of ten mice tested, NMDA (5 nmol) was administered intracerebroventricularly (i.c.v.). Under the conditions without pretreatment of the test compound, all of the mice exhibit tonic seizures. The number of mice which did not exhibit tonic seizures after i.c.v. administration of NMDA was counted as considered to be protected. Compound of Example 5 (30 mg/kg, i.p.) showed 90% protection from tonic seizures.

Reference Example 1

4-tert-Butoxycarbonylaminomethyl-2-methoxycarbonylm-ethylaniline 1) 4-Nitro-3-trifluoromethanesulfonyloxytoluene To a solution of 3-methyl-6-nitrophenol (3.06 g, 20 mmol) and 2,4,6-colidine (4.0 mL, 30 mmol) in dichloromethane (100 mL) was added slowly trifluoromethanesulfonic anhydride (7.05 g, 25 mmol) at room temperature. The mixture was stirred overnight at the same temperature, poured into water, and extracted with ethyl acetate. The organic layer was washed successively with 0.2N hydrochloric acid, water, saturated aqueous sodium bicarbonate, and brine, dried over magnesium sulfate, and concentrated to give 5.0 g of the title compound (88%): ¹H NMR (CDCl₃) δ8.03 (d, 1H, J=8.3 Hz), 7.36 (d, 1H, J=8.3 Hz), 7.24 (s, 1H), 2.52 (s, 3H).

2) 1-Nitro-4-phthalimidomethyl-2-trifluoromethanesulfonyloxybenzene

A mixture of 4-nitro-3-trifluoromethanesulfonyloxytoluene (5.7 g, 20 mmol), N-bromosuccinimide (5.7 g, 32 mmol), and benzoyl peroxide (1 g) in carbon tetrachloride (75 mL) was refluxed for 18 h. The insoluble material formed was removed by filtration and the filtrate was concentrated. The residue was dissolved in DMF (40 mL) and potassium phthalimide (2.6 g, 14 mmol) was added. The mixture was stirred for 5 h at room temperature, poured into brine, and extracted with a 1:1 mixture of toluene and ethyl acetate. The organic layers were washed with brine, dried over magnesium sulfate, and concentrated. The residue was purified by silica gel column chromatography with 9:1 to 1:1 hexane/ethyl acetate to give 3.4 g of the title compound (39%): 1H NMR (CDCl$_3$) δ8.14 (d, 1H, J=8.3 Hz), 7.86~7.91 (m, 2H), 7.75~7.79 (m, 2H), 7.63 (dd, 1H, J=8.3, 1.6 Hz), 7.54 (d, 1H, J=1.6 Hz), 4.93 (s, 2H).

3) Diethyl 2-nitro-5-phthalimidomethylphenylmalonate

To a suspension of 60% sodium hydride (5.8 g, 145 mmol) in DMF (150 mL) was added diethyl malonate (26.4 mL, 175 mmol) at room temperature, while the sodium hydride was washed with dry hexane before use. The mixture was heated at 40° C. for 1.5 h, allowed to cool at room temperature and 1-nitro-4-phthalimidomethyl-2-trifluoromethanesulfonyloxybenzene (25 g, 58 mmol) was added. The mixture was stirred overnight at room temperature, poured into 3% potassium hydrogen sulfate, and extracted with a 1:1 toluene/ethyl acetate. The extract was washed successively with 5% potassium hydrogen sulfate, water, saturated aqueous sodium bicarbonate, and brine, dried over magnesium sulfate, and concentrated. The unreacted diethyl malonate was distilled out in vacuo and the residual solid was washed with 1:1 diethyl ether/hexane to give 24.5 g of the title compound: $^1$H NMR (CDCl$_3$) δ8.04 (d, 1H, J=8.9 Hz), 7.85~7.90 (m, 2H), 7.72~7.78 (m, 2H), 7.56 (d, 1H, J=8.9 Hz), 7.54 (s, 1H), 5.24 (s, 1H), 4.90 (s, 2H), 4.27 (q, 4H, J=7.3 Hz), 1.28 (t, 6H, J=7.3 Hz).

4) Methyl 5-aminomethyl-2-nitrophenylacetate hydrochloride

A solution of diethyl 2-nitro-5-phthalimidomethylphenylmalonate in a mixture of concentrated hydrochloric acid (150 mL) and 1,4-dioxane (150 mL) was heated at 120° C. for 24 h. The solvents was removed in vacuo and the residual solid was dissolved in methanol (100 mL). To the solution was added thionyl chloride (11.8 g) at 0° C. The mixture was stirred for 2 h at 40° C. and the solvent and the excess reagent were removed in vacuo. The residue was washed with diethyl ether and dried to give 6.5 g of the title compound (quant): $^1$H NMR (CD$_3$OD) δ8.18 (d, 1H, J=8.6 Hz), 7.63 (dd, 1H, J=8.6, 1.6 Hz), 7.56 (d, 1H, J=1.6 Hz), 4.23 (s, 2H), 4.09 (s, 2H), 3.69 (s, 3H).

5) Methyl 5-tert-butoxycarbonylaminomethyl-2-nitrophenylacetate

To a solution of methyl 5-aminomethyl-2-nitrophenylacetate hydrochloride (6.80 g, 26.1 mmol) and triethylamine (12 mL) in dichloromethane (100 mL) was added di-tert-butyl dicarbonate (9 mL, 39.2 mmol) at room temperature. The mixture was stirred for 1.5 h and diluted with ethyl acetate. The mixture was washed successively with 5% potassium hydrogen sulfate, water, saturated aqueous sodium bicarbonate, and brine, dried over magnesium sulfate, and concentrated. The residue was purified by silica gel column chromatography with 6:1 to 2:1 hexane/ethyl acetate to give 8.55 g of the title compound (quant): $^1$H NMR (CDCl$_3$) δ8.11 (d, 1H, J=8.3 Hz), 7.38 (d, 1H, J=8.3 Hz), 7.25 (s, 1H), 4.98 (br, 1H), 4.39 (d, 2H, J=6.3 Hz), 4.02 (s,2H), 1.49 (s, 9H).

6) 4-tert-Butoxycarbonylaminomethyl-2-methoxycarbonylmethylaniline

A solution of methyl 5-tert-butoxycarbonylaminomethyl-2-nitrophenylacetate (6.8 g, 21 mmol) in methanol (250 mL) in the presence of 10% Pd/C was hydrogenated under atmospheric pressure of hydrogen at room temperature. The catalyst was removed by filtration through celite and the filtrate was concentrated to give 5.8 g of the title compound: $^1$H NMR (CDCl$_3$) δ 7.02 (d, 1H, J=7.6 Hz), 7.00 (s, 1H), 6.67 (d, 1H, J=7.6 Hz), 4.72 (br, 1H), 4.18 (d, 2H, J=5.7 Hz), 4.05 (br, 2H), 3.55 (s, 2H), 1.46 (s, 9H).

Reference Example 2

4-tert-Butoxycarbonylaminomethyl-2-tert-butoxycarbonylmethoxyaniline 1) 3-tert-Butoxycarbonylmethoxy-4-nitrotoluene A mixture of 3-methyl-6-nitrophenol (30.62 g, 200 mmol) and tert-butyl bromacetate (46.8 g, 240 mmol) in acetonitrile (700 mL) in the presence of potassium carbonate (69.1 g, 500 mmol) was refluxed for 2 h. Inorganic materials were removed by filtration and the filtrate was concentrated. The residue was diluted with ethyl acetate, washed with brine, dried over magnesium sulfate, and extensively concentrated in vacuo to give 54.2 g of the title compound (quant): $^1$H NMR (CDCl$_3$) δ7.82 (d, 1H, J=8.3 Hz), 6.87 (d, 1 H, J=8.3 Hz), 6.74 (s, 1H), 4.65 (s, 2H), 2.40 (s, 3H), 1.47 (s, 9H).

2) 4-Azidomethyl-2-tert-butoxycarbonylmethoxynitrobenzene

A mixture of 3-tert-butoxycarbonylmethoxy-4-nitrotoluene (36.1. g, 120 mmol), N-bromosuccinimide (21.3 g, 120 mmol), and benzoyl peroxide (4 g) in carbon tetrachloride (500 mL) was refluxed for 18 h. The insoluble material formed was removed by filtration and the filtrate was concentrated. The residue was dissolved in DMF (10 mL) and sodium azide (5.2 g, 80 mmol) was added. The mixture was stirred for 2 h at 50° C., poured into brine, and extracted with a 1:1 mixture of toluene and ethyl acetate. The organic layers were washed with brine, dried over magnesium sulfate, and concentrated. The residue was purified by silica gel column chromatography with 9:1 to 7:3 hexane/ethyl acetate to give 13.4 g of the title compound (36%): $^1$H NMR (CDCl$_3$) δ7.89 (d, 1H, J=8.3 Hz), 7.01 (dd, 1H, J=8.3, 1.7 Hz), 6.93 (d, 1H, J=1.7 Hz), 4.70 (s, 2H), 4.43 (s, 2H), 1.48 (s, 9H).

3) 4-tert-Butoxycarbonylaminomethyl-2-tert-butoxycarbonylmethoxyaniline

A solution of 4-azidomethyl-2-tert-butoxycarbonylmethoxynitrobenzene (2.96 g, 10 mmol) in ethyl acetate (50 mL) in the presence of di-tert-butyl dicarbonate (2.40 g, 11 mmol) and 10% Pd/C (1 g) was hydrogenated for 12 h under atmospheric pressure of hydrogen at room temperature. The catalyst was removed by filtration through celite and the filtrate was concentrated. The residue was purified by silica gel column chromatography with 3:1 to 1:1 hexane/ethyl acetate to give 1.75 g of the title compound (50%): $^1$H NMR (CDCl$_3$) δ6.73 (dd, 1H, J=8.3 Hz), 6.68 (d, 1H, J=8.3, 1.7 Hz), 6.66 (d, 1H, J=8.3 Hz), 4.65~4.75 (br, 1H), 4.52 (s, 2H), 4.16 (d, 2H, J=5.6 Hz), 3.90~4.00 (br, 2H), 1.49 (s, 9H), 1.46 (s, 9H).

Example 1

7-Chloro-1,3,4,5-tetrahydrobenz[cd]indole-2-carboxylic acid 1) 6-Nitrotetralin

To a suspension of 85% nitronium tetrafluoroborate (52 g, 0.333 mol) in dichloromethane (500 mL) was added dropwise a solution of tetralin (40 g, 0.303 mol) in dichloromethane (400 mL) over 45 min at 0° C. The mixture was stirred for 30 min at 0° C. and quenched by addition of ice-water (700 mL). The organic layer was separated, washed with water, dried over magnesium sulfate, and concentrated. The residue was purified by silica gel column chromatography with 30:1~5:1 hexane/toluene to give 14.15 g of the title compound: $^1$H NMR (CDCl$_3$) δ7.91 (s, 1H), 7.88 (d, 1H, J=7.6 Hz), 7.17 (d, 1H, J=7.6 Hz), 2.84 (m, 4H), 1.83 (m, 4H).

2) 6-Aminotetralin

To a solution of 6-nitrotetralin (11.5 g, 64.9 mmol) in a mixture of methanol (30 mL) and conc. HCl (40 mL) was added iron powder (11.35 g, 203.2 mmol) by portions over 1 h at room temperature. The mixture was stirred for 1 h at room temperature, poured into water (600 mL), neutralized to ca. pH 6 by addition of 1N aqueous sodium hydroxide, extracted with ethyl acetate (300 mL×2). Organic layers were washed with brine, dried over magnesium sulfate, and concentrated to give 9.45 g of the title compound: $^1$H NMR (CDCl$_3$) δ6.85 (d, 1H, J=8.1 Hz), 6.46 (dd, 1H, J=8.1, 2.5 Hz), 6.42 (s, 1H), 3.44 (bs, 2H), 2.65 (m, 4H), 1.75 (m, 4H).

3) 6-Chlorotetralin

To a mixture of cupric chloride (8.17 g, 60.76 mmol) and isopentyl nitrite (10.2 mL, 75.95 mmol) in acetonitrile (250 mL) was added a solution of 6-aminotetralin (9.30 g, 50.63 mmol) in acetonitrile (15 mL) at 0° C. over 10 min. The mixture was stirred for 2 h at room temperature, quenched by addition of 18% aqueous HCl, and extracted with diethyl ether (300 mL×2). The organic layers were washed successively with 18% hydrochloric acid, water, and brine, dried over magnesium sulfate, and concentrated. The residue was purified by silica gel column chromatography with 30:1 hexane/ethyl acetate to give 6.07 g of the title compound (72%): $^1$H NMR (CDCl$_3$) δ7.02 (m, 2H), 6.94 (d, 1H, J= 8.9 Hz), 2.90 (m, 4H), 1.76 (m, 4H).

4) 7-chloro-5-nitrotetralin

To a suspension of 85% nitronium tetrafluoroborate (6.19 g, 39.6 mmol) in dichloromethane (60 mL) was added dropwise a solution of 6-chlorotetralin (6.0 g, 36 mmol) in dichloromethane (60 mL) over 15 min at 0° C. The mixture was stirred for 40 min at 0° C. and quenched by addition of ice-water (100 mL). The organic layer was separated, washed with water, dried over magnesium sulfate, and concentrated. The residue was purified by silica gel column chromatography with 30:1~4:1 hexane/toluene to give 3.83 g of the title compound (54%): $^1$H NMR (CDCl$_3$) δ7.65 (d, 1H, J=2.3 Hz), 7.30 (d, 1H, J=8.9 Hz), 2.90 (m, 4H), 1.76 (m, 4H).

5) 6-Chloro-1-ethoxalyl-8-nitrotetralin

To a mixture of potassium t-butoxide (79.49 g, 0.708 mol) and diethyl oxalate (105.8 mL, 0.779 mol) in ethanol (140 mL) was added 7-chloro-5-nitrotetralin (14 g, 0.071 mol) at room temperature. The mixture was stirred for 2 h, poured into 10% aqueous KHSO$_4$, and extracted with ethyl acetate (400 mL×2). The combined organic layers were washed successively with water and brine, dried over magnesium sulfate, and concentrated. The residue was purified by silica gel column chromatography with 15:1~6:1 hexane/-ethyl acetate to give 8.39 g of the title compound: $^1$H NMR (CDCl$_3$) δ7.91 (d, 1H, J=2.1 Hz), 7.45 (d, 1H, J=6.3, 4.0 Hz), 4.41 (m, 2H), 2.82~3.09 (m, 2H), 2.02 (m, 2H), 1.85 (m, 2H), 1.42 (t, 3H, J=7.3 Hz).

6) 7-Chloro-1,3,4,5-tetrahydrobenz[cd]indole-2-carboxylic acid

To a mixture of aqueous 20% TiCl$_3$ (145 g, 0.188 mol), water (150 mL), and acetone (150 mL) was added dropwise a solution of 6-chloro-1-ethoxalyl-8-nitrotetralin (8.39 g, 0.027 mol) in acetone (150 mL) at 0° C. The mixture was stirred for 1 h at room temperature, diluted with water, and extracted with ethyl acetate (400 mL×2). The combined organic layers were washed successively with water and brine, dried over magnesium sulfate, and concentrated. The residue was dissolved in a mixture of THF (60 mL) and MeOH (60 mL) and 1N NaOH (60 mL) was added. The mixture was stirred for 2 h at room temperature, washed with diethyl ether (600 mL), acidified to pH 3 by using aqueous 5% KHSO4 and extracted with ethyl acetate (400 mL×2). The combined organic layers were washed successively with water and brine, dried over magnesium sulfate, and concentrated to give 2.07 g of the title compound: $^1$H NMR (CDCl$_3$) δ8.57 (bs, 1H), 7.18 (s, 1H), 6.86 (s, 1H), 3.14 (t, 2H, J=6.1 Hz), 2.91 (t, 2H, J=6.1 Hz), 2.10 (m, 2H).

Example 2

Methyl 7-chloro-1,3,4,5-tetrahydrobenz[cd]indole-2-carboxylate

To a solution of 7-chloro-1,3,4,5-tetrahydrobenz[cd]indole-2-carboxylic acid (8 g) in MeOH (100 mL) was added thionyl chloride (6.2 mL) at 0° C. The mixture was refluxed for 13 h, while thionyl chloride (10 mL×4) was added during the reflux. The resulting mixture was concentrated and the residue was purified by silica gel column chromatography with 15:1~1:1 hexane/ethyl acetate to give 2.47 g of the title compound (37%): $^1$H NMR (CDCl$_3$) δ8.52 (bs, 1H), 7.15 (d, 1H, J=1.5 Hz), 6.84 (d, 1H, J=1.5 Hz), 3.93 (s, 3H), 3.07 (t, 2H, J=6.3 Hz), 2.90 (t, 2 H, J=6.3 Hz), 2.07 (5et, 2H, J=6.3 Hz).

Example 3

7-Chloro-3-carboxymethyl-1,3,4,5-tetrahydrobenz[cd]indole-2-carboxylic acid 1) Methyl 1-benzenesulfonyl-7-chloro-1,3,4,5-tetrahydrobenz[cd]indole-2-carboxylate To a suspension of sodium hydride (60%, 0.96 g, 40 mmol) in THF (5 mL) was added a solution of methyl 7-chloro-1,3,4,5-tetrahydrobenz[cd]-indole-2-carboxylate (2.40 g, 9.61 mmol) in THF (20 mL) at 0° C. The mixture was stirred for 10 rain and benzenesulfonyl chloride (2.04 g, 11.5 mmol) was added. The resulting mixture was stirred for 8 h at room temperature, diluted with saturated ammonium chloride, and extracted with ethyl acetate (400 mL×2). The combined organic layers were washed successively with water and brine, dried over magnesium sulfate, and concentrated. The residue was purified by silica gel column chromatography with 7:1~1:1 hexane/toluene to give 2.52 g of the title compound (67%): $^1$H NMR (CDCl$_3$) δ7.99 (dd, 2H, J=8.4, 1.3 Hz), 7.90 (d, 1H, J=1.3 Hz), 7.48~7.63 (m, 3H), 7.04 (d, 1H, J=1.3 Hz), 3.88 (s, 3H), 2.91 (t, 2H, J=5.9 Hz), 2.84 (t, 2H, J=5.9 Hz), 1.98 (5 et, 2 H, J=5.9 Hz).

2) Methyl 1-benzenesulfonyl-7-chloro-3-(di-t-butoxycarbonyl)methyl-1,3,4,5-tetrahydrobenz[cd]inodole- 2-carboxylate A mixture of methyl 1-benzenesulfonyl-7-chloro-1,3,4,5-tetrahydrobenz[cd]-indole-2 -carboxylate (2.30 g), N-bromosccinimide (1.16 g, 6.49 mmol) in carbon tetrachloride (50 mL) in the presence of a catalytic amount of azoisobutyronitorile was refluxed for 1 h. Insoluble materials were filtered off and the filtrate was concentrated. The residue was dissolved in DMF (30 mL) and added dropwise at room temperature to a solution of anion of di-t-butyl malonate in DMF (5 mL) prepared by reaction of di-t-butyl malonate (1.45 mL, 6.49 mmol) with sodium hydride (60%, 0.248 g, 6.19 mmol) at 50° C. for 1 h. The mixture was stirred for 3 h at room temperature, acidified to pH 3 with 5% KHSO$_4$, and extracted with a 1:1 mixture of ethyl acetate and toluene. The organic layer was washed successively with water and brine, dried over magnesium sulfate, and concentrated. The residue was purified by silica gel column chromatography with 8:1~6:1 hexane/toluene to give 1.53 g of the title compound (44%): $^1$H NMR (CDCl$_3$) δ8.02 (dd, 2H, J=7.6, 1.3 Hz), 7.90 (s, 1H), 7.55 (td, 1H, J=7.6, 1.3 Hz), 7.49 (td, 2H, J=7.6, 1.3 Hz), 7.05 (s, 1H), 3.96 (m, 1H), 3.94 (s, 3H), 3.47 (d, 1H, J=9.6 Hz), 3.01 (ddd, 1H, J=1.72, 11.7, 4.3 Hz), 2.81 (ddd, 1H, J=17.2, 5.3, 4.0 Hz), 2.81 (m, 1H), 1.97 (m, 1H), 1.37 (s, 9H), 1.22 (s, 9H).

3) Methyl 1-benzenesulfonyl-7-chloro-3-(di-carboxy)methyl-1,3,4,5-tetrahydrobenz[cd]indole-2-carboxylate A mixture of methyl 1-benzenesulfonyl-7-chloro-3-(di-t-butoxy-carbonyl)methyl-1,3,4,5-tetrahydrobenz[cd]indole-2-carboxylate (1.51 g, 2.55 mmol) and p-toluenesulfonic acid monohydrate (0.15 g) in toluene (30 mL) was refluxed for 8 h, diluted with water, and extracted with a mixture of ethyl acetate and THF. The organic layer was washed successively with water and brine, dried over magnesium sulfate, and concentrated. The residue was rinsed with dichloromethane and dried in vacuo to give 0.77 g of the title compound (63%): $^1$H NMR (CD$_3$OD) δ7.89 (dd, 2H, J=7.3, 1.3 Hz), 7.79 (s, 1H), 7.63 (td, 1H, J= 7.6, 1.3 Hz), 7.52 (td, 2H, J=7.3, 1.3 Hz), 7.11 (s, 1H), 3.94 (m, 1H), 3.89 (s, 3H), 3.57 (d, 1H, J=8.3 Hz), 3.01 (ddd, 1H, J=17.2, 11.7, 4.3 Hz), 2.81 (m, 1H), 2.26 (ddd, 1H, J=3.9, 7.4, 4.0 Hz), 1.92 (m, 1H).

4) Methyl 1-benzenesulfonyl-7-chloro-3-carboxymethyl-1,3,4,5-tetrahydrobenz[cd]indole-2-carboxylate A solution of methyl 1-benzenesulfonyl-7-chloro-3-(dicarboxy)-methyl-1,3,4,5-tetrahydrobenz[cd]indole-2-carboxylate (0.77 g, 1.61 mmol) in acetic acid (50 mL) was refluxed for 3 h and concentrated. The residue was rinsed with dichloromethane and dried in vacuo to give 0.59 g of the title compound (84%): $^1$H NMR (DMSO-d$_6$) δ12.2 (bs, 1H), 7.99 (d, 2H, J=7.6 Hz), 7.79 (s, 1H), 7.74 (t, 1H, J=7.6 Hz), 7.65 (t, 2H, J=7.6 Hz), 7.22 (s, 1H), 3.83 (s, 3H), 3.56 (m, 1H), 2.86 (m, 2H), 2.44 (d, 2H, J=10.2 Hz), 2.01 (m, 1 H), 1.84 (m, 1H).

5) 7-Chloro-3-carboxymethyl-1,3,4,5-tetrahydrobenz[cd]indole-2-carboxylic acid

A solution of methyl 1-benzenesulfonyl-7-chloro-3-carboxymethyl-1,3,4,5-tetrahydrobenz[cd]indole-2-carboxylate (143 mg, 0.328 mmol) in a mixture of THF (2 mL), MeOH (2 mL), and 5N NaOH (2 mL) was stirred for 19 h at room temperature, acidified to pH 3 with 5% KHSO$_4$, and extracted with ethyl acetate. The organic layer was washed successively with water and brine, dried over magnesium sulfate, and concentrated. The residue was rinsed with dichloroethane and dried in vacuo to give 56 mg of the title compound (58%): $^1$H NMR (DMSO-d$_6$) δ12.58 (bs, 1H), 11.45 (s, 1H), 7.14 (d, 1H, J=1.0 Hz), 6.83 (d, 1H, J=1.0 Hz), 3.76 (m, 1H), 2.93 (mt, 1H, J=12.7 Hz), 2.78 (md, 1H, J=15.8 Hz), 2.64 (dd, 1H, J=15.3, 3.0 Hz), 2.35 (dd, 1H, J=15.5, 11.5 Hz), 2.08 (md, 1H, J=12.2 Hz), 1.87 (m, 1H).

Example 4

7-Chloro-3-[p-tert-butoxycarbonylaminomethyl-o-(carboxymethyl)phenylcarbamoylmethyl]-1,3,4,5-tetrahydrobenz[cd]indole-2-carboxylic acid 1) Methyl 1-benzenesulfonyl-7-chloro-3-[p-tert-butoxycarbonylaminomethyl-o-(methoxycarbonylmethyl)phenylcarbamonylmethyl]-1,3,4,5,-tetrahydrobenz[cd]-indole-2-carboxylate A mixture of 4-tert-butoxycarbonylaminomethyl-2-methoxycarbonylmethylaniline (129 mg, 0.459 mmol), methyl 1-benzenesulfonyl-7-chloro-3-carboxymethyl-1,3,4,5-tetrahydrobenz[cd]indole-2-carboxylate (200 mg, 0.414 mmol), triethylamine (0.16 mL, 1.15 mmol), and N,N-bis(2-oxo-3-oxazolidinyl)-phosphinic chloride (Bop-Cl, 128 mg, 0.505 mmol) in dichloromethane (4 mL) was stirred for 20 h at room temperature and diluted with ethyl acetate. The mixture was washed successively with 5% potassium hydrogen sulfate, water, 0.1M phosphate buffer (pH 7), water, and brine, dried over magnesium sulfate, and concentrated. The residue was purified by silica gel column chromatography with 1:1 hexane/ethyl acetate to give 325 mg of the title compound (98%): $^1$H NMR (CDCl$_3$) δ8.82 (s, 1H), 8.01 (dd, 2H, J=7.6, 1.3 Hz), 7.91 (s, 1H), 7.80 (d, 1H, J=8.3 Hz), 7.58 (td, 1H, J=7.6, 1.3 Hz), 7.51 (td, 2H, J=7.6, 1.3 Hz), 7.20 (d, 1H, J=8.3 Hz), 7.12 (s, 1H), 7.08 (s, 1H), 5.00 (br, 1H), 4.25 (d, 2H, J=5.9 Hz), 3.87 (s, 3H), 3.86 (m, 1H), 3.67 s,3 H), 3.58 (d, 1H, J=14.5 Hz), 3.52 (d, 1H, J=14.5 Hz), 3.02 (mt, 1H, J=1.30 Hz), 2.83 (md, 1H, J=13.5 Hz), 2.76 (dd, 1H, J=14.2, 3.3 Hz), 2.51 (dd, 1H, J=14.2, 10.2 Hz), 2.22 (md, 1H, J=10.5 Hz), 2.01 (m, 1H), 1.45 (s, 9H).

2) 7-Chloro-3-[p-tert-butoxycarbonylaminomethyl-o-(carboxymethyl)phenylcarbamoylmethyl]-1,3,4,5-tetrahydrobenz[cd]indole-2-carboxylic acid A solution of methyl 1-benzenesulfonyl-7-chloro-3-[p-tert-butoxycarbonylaminomethyl-o-(methoxycarbonylmethyl)phenylcarbamoylmethyl]-1,3,4,5-tetrahydrobenz[cd]indole-2-carboxylate (300 mg, 0.414 mmol) in a mixture of THF (5 mL), MeOH (5 mL), and 1N LiOH (5 mL) was stirred for 19 h at room temperature, acidified to pH 3 with 5% KHSO$_4$, and extracted with ethyl acetate. The organic layer was washed successively with water and brine, dried over magnesium sulfate, and concentrated. The residue was rinsed with diethyl ether and dried in vacuo to give 150 mg of the title compound (quant): $^1$H NMR (DMSO-d$_6$) δ12.54 (br, 2H), 11.42 (s, 1H), 9.33 (s, 1H), 7.37 (d, 1H, J=7.9 Hz), 7.35 (s, 1H), 7.13 (d, 1H, J=7.9 Hz), 7.10 (s, 2H), 6.83 (s, 1H), 4.08 (d, 2H, J=7.9 Hz), 3.88 (m, 1H), 3.59 (d, 1H, J=16.3 Hz), 3.55 (d, 1H, J=16.3 Hz), 3.09 (mr, 1H, J=14.0 Hz), 2.81 (md, 1H, J=16.8 Hz), 2.64 (dd, 1H, J=14.0, 3.5 Hz), 2.53 (m, 1H), 2.09 (md, 1, H, J=12.2 Hz), 1.83 (m, 1H), 1.40 (s, 9H).

Example 5

7-Chloro-3-[p-aminomethyl-o-(carboxymethyl)phenylcarbamoylmethyl]-1,3,4,5-tetrahydrobenz[cd]indole-2-carboxylic acid hydrochloride A solution of 7-chloro-3-[p-tert-butoxycarbonylaminomethyl-o(carboxymethyl)phenylcarbamoylmethyl]- 1,3,4,5-tetrahydrobenz[cd]indole-2-carboxylic acid (150 mg) in a mixture of 1,4-dioxane (4 mL) and 4N HCl in 1,4-dioxane (4 mL) was stirred for 24 h at room temperature and concentrated in vacuo. The residue was rinsed with diethyl ether and dried in vacuo to give 103 mg of the title compound (quant): $^1$H NMR (DMSO-d$_6$) δ11.44 (s, 1H), 9.49 (s, 1H), 8.35 (br, 3H), 7.52 (d, 1 H, J=8.3 Hz), 7.37 (d, 1H, J=8.3 Hz), 7.35 (s, 1H), 7.16 (s, 1H), 6.83 (s, 1H), 3.97 (bs, 2H), 3.89 (m, 1H), 3.68 (d, 1H), J=16.5 Hz), 3.60 (d, 1H, J=16.5 Hz), 3.11 (mt, 1H, J=14.5 Hz), 2.80 (md, $^1$H, J=17.2 Hz), 2.60 (m, 2H), 2.09 (md, 1H, J=12.9 Hz), 1.82 (m, 1H).

Example 6

7-Chloro-3-phenylcarbamoylmethyl-1,3,4,5-tetrahydrobenz[cd]indole-2-carboxylic acid 1) Methyl 1-benzenesulfonyl-7-chloro-3-phenylcarbamoylmethyl-1,3,4,5-tetrahydrobenz[cd]indole-2-carboxylate A mixture of aniline (27.4 mg, 0.303 mmol), methyl 1-benzenesulfonyl-7-chloro-3-carboxymethyl-1,3,4,5-tetrahydrobenz[cd]indole-2-carboxylate (120 mg, 0.275 mmol), 1-hydroxy-benzotriazole (46 mg, 0.303 mmol), and 1-ethyl-3-(3-dimethylaminopropyl)carbodiimide (47 mg, 0.303 mmol) in DMF (2.5 mL) was stirred for 20 h at room temperature, acidified to pH 1 by adding 1N HCl, and extracted with 1:1 toluene/ethyl acetate. The organic layer was washed successively with 1N HCl, water, saturated sodium bicarbonate, water, and brine, dried over magnesium sulfate, and concentrated to give 161 mg of the title compound (quant): $^1$H NMR (CDCl$_3$) δ7.95 (d, 2H, J=7.3 Hz), 7.90 (s, 1H), 7.85 (s, 1H), 7.58 (t, 1H, J=7.3 Hz), 7.52 (d, 1H, J=8.3 Hz), 7.46 (t, 1H, J=8.3 Hz), 7.30 (t, 1H, J=8.3 Hz), 7.15 (t, 1H, J=7.05 (s, 1H), 3.84 (s, 3H), 3.71 (m, 1H), 2.92 (ddd, 1H, J=17.2, 12.2, 3.6 Hz), 2.80 (md, 1H, J=17.2 Hz), 2.65 (dd, 1H, J=14.2, 4.0 Hz), 2.47 (dd, 1H, J=14.2, 9.6 Hz), 2.19 (md, 1H, J=13.6 Hz), 1.89 (m, 1H).

2) 7-Chloro-3-phenylcarbamoylmethyl-1,3,4,5-tetrahydrobenz[cd]indole-2-carboxylic acid A solution of methyl 1-benzenesulfonyl-7-chloro-3-phenylcarbamoylmethyl-1,3,4,5-tetrahydrobenz[cd]indole-2-carboxylate (140 mg, 0.268 mmol) in a mixture of THF (3 mL), MeOH (3 mL), and 5N NaOH (3 mL) was stirred for 22 h at room temperature, acidified to pH 1 with 1N HCl, and, extracted with 1:1 THF/ethyl acetate. The organic layer was washed successively with water and brine, dried over magnesium sulfate, and concentrated. The residue was rinsed with dichloromethane and dried in vacuo to give 64 mg of the title compound (63%): $^1$H NMR (DMSO-d$_6$) δ5 12.92 (bs, 1H), 11.44 (s, 1H), 9.86 (s, 1H), 7.60 (d, 2H, J=7.3 Hz), 7.30 (t, 2H, J=7.3 Hz), 7.16 (s, 1H), 7.03 (t, 1H, J=7.3 Hz), 6.85 (s, 1H), 3.89 (m, 1H), 3.06 (mt, 1H, J=12.6 Hz), 2.79 (md, 1H, J=16.8 Hz), 2.68 (dd, 1H, J=14.2, 4.3 Hz), 2.50 (m, 1H), 2.06 (md, 1H, J=12.2 Hz), 1.85 (m, 1H).

Example 7

7-Chloro-3-[p-tert-butoxycarbonylaminomethyl-o-(carboxymethoxy)phenylcarbamoylmethyl]-1,3,4,5 -tetrahydrobenz[cd]indole-2-carboxylic acid 1) Methyl 1-benzenesulfonyl-7-chloro-3-[ p-tert-butoxycarbonylaminomethyl-o-(tert-butoxycarbonylmethoxy)phenylcarbamoylmethyl]-1,3,4,5 -tetrahydrobenz[cd]indole-2-carboxylate A mixture of 4-tert-butoxycarbonylaminomethyl-2-tert-butoxycarbonylmethoxyaniline (202 mg, 0.574 mmol), methyl 1-benzenesulfonyl-7-chloro-3 -carboxymethyl-1,3,4,5-tetrahydrobenz[cd]indole-2-carboxylate (250 mg, 0.574 mmol), triethylamine (0.2 mL, 1.43 mmol), and N,N-bis(2-oxo-3 -oxazolidinyl)-phosphinic chloride (Bop-Cl, 161 mg, 0.631 mmol) in dichloromethane (5 mL) was stirred for 15 h at room temperature and diluted with ethyl acetate. The mixture was washed successively with 5% potassium hydrogen sulfate, water, saturated sodium bicarbonate, water, and brine, dried over magnesium sulfate, and concentrated to give 463 mg of the title compound (quant): $^1$H NMR (CDCl$_3$) δ8.63 (s, 1H), 8.33 (d, 1H, J=8.6 Hz), 8.03 (d, 2H, J=6.9 Hz), 7.92 (s, 1H), 7.58 (t, 1H, J=6.9 Hz); 7.52 (t, 2H, J=6.9 Hz), 7.06 (s, 1H), 6.94 (d, 1H, J=Hz), 6.80 (s, 1H), 4.82 (br, 1H), 4.35 (s, 2H), 4.12 (d, 2H, J=7.3 Hz), 3.89 (s, 3H), 3.86 (m, 1H), 3.03 (mt, 1H, J=14.7 Hz), 2.81 (m, 1H), 2.81 (dd, 1H, J=14.7, 4.3 Hz), 2.53 (dd, 1H, J=14.7, 10.4 Hz), 2.22 (m, 1H), 1.72 (m, 1H), 1.46 (s, 9H), 1.45 (s, 9H).

2) 7-Chloro-3-[p-tert-butoxycarbonylaminomethyl-o-(carboxymethoxy)phenylcarbamoylmethyl]-1,3,4,5 -tetrahydrobenz[cd]indole-2-carboxylic acid A solution of methyl 1-benzenesulfonyl-7-chloro-3-[p-tert-butoxycarbonylaminomethyl-o-(tert-butoxycarbonylmethoxy)phenylcarbamoylmethyl]-1,3,4,5 -tetrahydrobenz[cd]indole-2-carboxylate (410 mg, 0.532 mmol) in a mixture of THF (6 mL ), MeOH (6 mL), and 1N LiOH (6 mL) was stirred for 17 h at room temperature, acidified to pH 2 with 5% KHSO$_4$, and extracted with ethyl acetate. The organic layer was washed successively with water and brine, dried over magnesium sulfate, and concentrated. The residue was rinsed with diethyl ether and dried in vacuo to give 195 mg of the title compound (quant): $^1$H NMR (DMSO-d$_6$) δ13.01 (br, 2H), 11.43 (s, 1H), 9.13 (s, 1H), 7.90 (d, 1H, J=8.3 Hz), 7.33 (d, 1H, J=6.3 Hz), 7.15 (s, 1H), 6.84 (s, 2H), 6.82 (d,1H, J= 8.3 Hz), 4.05 (d, 2H, J=6.3 Hz), 3.88 (m, 1H), 3.32 (bs, 2H), 3.09 (mt, 1H, J= 12.2 Hz), 2.79 (md, 1H, J=17.8 Hz), 2.68 (bd, 1H, J=13.9 Hz), 2.61 (bd, 1H, J=13.9 Hz), 2.09 (md 1H, J=14.2 Hz), 1.84 (m, 1H), 1.40 (s, 9H).

Example 8

7-Chloro-3-[p-aminomethyl-o-(carboxymethoxy)phenylcarbamoylmethyl]-1,3,4,5 -tetrahydrobenz[cd]indole-2-carboxylic acid hydrochloride A solution of 7-chloro-3-[ p-tert-butoxycarbonylaminomethyl-o-(carboxymethoxy)phenylcarbamoylmethyl]-1,3,4,5 -tetrahydrobenz[cd]indole-2-carboxylic acid acid (189 mg)in a mixture of 1,4-dioxane (4 mL) and 4N HCl in 1,4-dioxane (4 mL) was Stirred for 20 h at room temperature and concentrated in vacuo. The residual solid was rinsed with THF and dried in vacuo to give 104 mg of the title compound (47%): $^1$H NMR (DMSO-d$_6$) δ13.05 (br, 2H), 11.45 (s, 1H), 9.24 (s, 1H), 830 (br, 3H), 8.04 (d, 1H, J=8.3 Hz), 7.20 (s, 1H), 7.16 (s, 1H), 7.06 (d, 1H, J=8.3 Hz), 6.84 (s, 1H), 4.74 (s, 2H), 3.90 ~3.95 (m,3H), 3.09 (m, 1H), 2.78 (m1H), 2.69 (m, 2H), 2.08 (m, 1H), 1.85 (m, 1H).

Example 9

7-Chloro-3-tert-butoxycarbonylmethyl-1,3,4,5-tetrahydrobenz[cd]indole-2-carboxylic acid methyl ester 1) 2-Amino-4-chlorotoluene To a solution of 2-nitro-4-chlorotoluene (86 g, 0.5 mol) in MeOH (250 mL) was added Fe powder (92 g, 3.65 mol) by portions over 45 min while refluxing gently. The mixture was stirred for 3 h at room temperature, poured into water (1.5 L) and extracted with AcOEt. The organic layers were dried over MgSO$_4$ and concentrated in vacuo to give 63 g of the title compound.

2) 4-Chloro-2-(3-oxopropyl)toluene

To a suspension of 2-amino-4-chlorotoluene (1.41 g, 10 mmol) in 24% aq. HCl (5 mL) Was added dropwise NaNO$_2$ (710 mg, 1.03 mmol) in H$_2$O (3 mL) over 30 min at 0° C. The resulting solution was added dropwise to a solution of acrolein (1 mL, 15 mmol) in a mixture of DMF (15 mL) and 20% aq. TiCl$_3$ (20 mL, 26 mmol). After the addition was completed, the mixture was stirred for 30 min at room temperature and extracted with diethyl ether. The extracts was dried over MgSO$_4$ and concentrated. The residue was purified by silica gel column chromatography with 5:1 hexane/AcOEt to give 1.11 g of the title compound (60%): $^1$H NMR (CDCl$_3$) δ9.83 (s, 1H), 7.06~7.12 (m, 3H), 2.90 (t, 2H, J=7.2 Hz), 2.74 (t, 2H, J=7.2 Hz), 2.27 (s, 3H).

3) 4-Chloro-2-(3-hydroxypropyl)toluene

To a solution of 4-chloro-2-(3-oxopropyl)toluene in MeOH was added excess NaBH$_4$ at room temperature and the mixture was diluted with water, treated with 1N HCl, and extracted with AcOEt. The extracts was dried and concentrated to give quantitatively the title compound: $^1$H NMR (CDCl$_3$) δ7.14 (bd, 1H, J=9 Hz), 7.06 (d, 1H, J=9 Hz), 7.05 (bs, 1H), 3.66~3.77 (m, 2H), 2.68 (t, 2H, J=7.2 Hz), 2.30 (s, 3H), 1.83 (5et, 2H, J=7.2 Hz), 1.35~1.44 (br, 1H).

4) 2-(3-Acetoxypropyl)-4-chloro-toluene

To a solution of 4-chloro-2-(3-hydroxypropyl)toluene (3.7 g, 20 mmol), triethylamine (40 mmol) and 4-dimethylaminopyridine (4 mmol) in dichloromethane (20 mL) was added acetic anhydride (15 mmol) at 0° C. The mixture was stirred for ca. 1 h at 0° C., diluted with water, and extracted with AcOEt. The extract was washed with diluted aqueous HCl and brine, dried over $MgSO_4$, and concentrated to give quantitatively the title compound: $^1H$ NMR ($CDCl_3$) δ7.11 (bs, 1H), 7.07 (bs, 2H), 4.07 (t, 2H, J=7.2 Hz), 2.65 (dd, 2H, J=7.2, 8.1 Hz), 2.28 (s, 3H), 2.05 (s, 3H), 1.84–1.96 (m, 2H).

5) 2-(3-Acethoxypropyl)-4-chloro-6-nitrotoluene

To a solution of 2-(3-hydroxypropyl)-4-chloro-toluene (6.2 g, 33.5 mmol) and triethylamine (9.34 mL, 67 mmol) in dichloromethane (25 mL) was added acetic anhydride (5.1 mL, 50.3 mmol) at room temperature. The mixture was stirred for 2 h and concentrated in vacuo. The residue was diluted with aq. $KHSO_4$ and extracted with AcOEt. The extracts were dried and concentrated. The residue was dissolved in dichloromethane (50 mL). $NO_2^+BF_4^-$ (5.77 g, 36.85 mmol) was added at 0° C. The mixture was stirred for 30 min at 0° C. and poured into water. The mixture was extracted with AcOEt and the extracts was dried and concentrated. The residue was purified by silica gel column chromatography with 5:1 hexane/AcOEt to give 5.0 g of the title compound: $^1H$ NMR ($CDCl_3$) δ7.63 (bs, 1H), 7.36 (bs, 1H), 4.13 (t, 2H, J=7.2 Hz), 2.78 (t, 2H, J=7.2 Hz), 2.41 (s, 3H), 2.09 (s, 3H), 1.89–2.01 (m, 2H).

6) 3-Chloro-5-(3-hydroxypropyl)-6-methoxalylmethylnitrobenzene

To a mixture of dimethyl oxalate (107.6 g, 0.910 mol) and 30% potassium methoxide in methanol (194 g, 0.828 mol) was added 2-(3-acethoxypropyl)-4-chloro-6-nitrotoluene (22.0 g, 0.081 mol) at room temperature. The mixture was stirred for 4 h at the same temperature, poured into aq. $KHSO_4$ and extracted with EtOAc. The extracts were washed with brine, dried over $MgSO_4$ and concentrated. The residue was purified by silica gel column chromatography with 3:2 to 1:2 hexane/toluene to give 19.91 g of the title compound (78%): $^1H$ NMR ($CDCl_3$) δ7.91 and 7.75 (d, 1H, J=2.3 Hz), 7.54 and 7.41 (d, 1H, J=2.3 Hz), 4.51 (s, 1H), 3.95 (s, 3H), 3.65 (t, 2H, J=5.8 Hz), 2.78 (m, 2H), 1.84 (m, 2H).

7) 6-Chloro-4-(3-hydroxypropyl)indole-2-carboxylic acid methyl ester

To a solution of 3-chloro-5-(3-hydroxypropyl)-6-methoxalylmethylnitrobenzene (19.91 g, 0.063 mol) in acetone (300 mL) was added dropwise a mixture of 20% $TiCl_3$ (340 g, 0.441 mol), water (300 mL), and acetone (300 mL) at room temperature over a period of 30 min. The mixture was stirred for 30 min at room temperature and extracted with AcOEt. The extracts were washed with brine, dried over $MgSO_4$ and concentrated. The residue was purified by silica gel column chromatography with 4:1 to 1:2 hexane/toluene to give 11.39 g of the title compound (68%): $^1H$ NMR ($CDCl_3$) δ8.96 (bs, 1H), 7.27 (s, 1H), 7.26 (d, 1H, J=1.7 Hz), 6.97 (d, 1H, J=1.7 Hz), 3.95 (s, 3H), 3.71 (t, 2H, J=6.3 Hz), 2.98 (t, 2H, J=7.8 Hz), 2.00 (m, 2H).

8) 6-Chloro-4-(3-oxopropyl)indole-2-carboxylic acid methyl ester

To a solution of dimethyl sulfoxide (3.5 mL, 49.3 mmol) in dichloromethane (150 mL) was added dropwise oxalyl chloride (4.3 mL, 49.3 mmol) at −78° C. and the mixture was stirred for 20 rain at the same temperature. To the mixture was added dropwise a solution of 6-chloro-4-(3-hydroxypropyl)indole-2-carboxylic acid methyl ester (11.0 g, 41.1 mmol) in dichloromethane (1350 mL) at −78° C. over a period of 2 h. The mixture was stirred for 1 h at −78° C. and triethylamine (17.2 mL, 123.3 mmol) was added slowly at the same temperature. The mixture was allowed to warm at room temperature, diluted with water, and the organic layer was separated. The layer was washed with water, dried over $MgSO_4$, and concentrated to give 12.24 g of the title compound (quant): $^1H$ NMR ($CDCl_3$) δ9.86 (t, 1H, J=1.0 Hz), 9.06 (bs, 1H), 7.29 (d, 1H, J=1.3 Hz), 7.22 (d, 1H, J=1.7 Hz), 6.96 (d, 1H, J=1.7 Hz), 3.96 (s, 3H), 3.20 (t, 2H, J=7.4 Hz), 2.90 (t, 2H, J=7.4 Hz).

9) 6-Chloro-4-(4-tert-butoxycarbonyl-3-butenyl)indole-2-carboxylic acid methyl ester A mixture of 6-chloro-4-(3-oxopropyl)indole-2-carboxylic acid methyl ester (12.0 g, 45.2 mmol) and (tert-butoxycarbonylmethylene)triphenylenephosphorane (18.7 g, 49.7 mmol) in toluene (500 mL) was refluxed for 1 h and concentrated. The residue was purified by silica gel column chromatography with 5:1 hexane/toluene to give 12.21 g of the title compound (82%): $^1H$ NMR ($CDCl_3$) δ9.03 (bs, 1H), 7.29 (d, 1H, J=1.7 Hz), 7.20 (d, 1H, J=2.0 Hz), 6.95 (d, 1H, J=2.0 Hz), 6.92 (dt, 1H, J=15.5, 6.6 Hz), 5.80 (dt, 1H, J=15.5, 1.7 Hz), 3.96 (s, 3H), 3.01 (dd, 2H, J=8.6, 7.3 Hz), 2.59 (dd, 2H, J=14.5, 6.6 Hz), 1.49 (s, 9H).

10) 3-Bromo-6-chloro-4-(4-tert-butoxycarbonyl-3-butenyl)indole-2-carboxylic acid methyl ester To a solution of 6-chloro-4-(4-tert-butoxycarbonyl-3-butenyl)indole-2-carboxylic acid methyl ester (12.0 g, 33 mmol) in DMF (120 mL) was added slowly a solution of NBS (5.87 g, 33 mmol) in DMF (60 mL) at 0° C. The mixture was stirred for 1 h at 0° C., diluted with aqueous $NaHCO_3$, and extracted with 2:1 ethyl acetate/toluene. The extract was washed with water and brine, dried over $MgSO_4$, and concentrated. The residue was purified by silica gel column chromatography with 8:1 to 5:1 hexane/ethyl acetate to give 13.3 g of the title compound (91%): $^1H$ NMR ($CDCl_3$) δ9.15 (bs, 1H), 7.28 (d, 1H, J=1.8 Hz), 6.97 (dt, 1H, J=15.8, 6.9 Hz), 6.93 (d, 1H, J=1.8 Hz), 5.83 (dt, 1H, J=15.8, 1.7 Hz), 3.99 (s, 3H), 3.32 (dd, 2H, J=8.3, 7.9 Hz), 2.57 (m, 2H), 1.50 (s, 9H).

11) 7-Chloro-3-(tert-butoxycarbonylmethylene)-1,4,5-trihydrobenz[cd]indole-2-carboxylic acid methyl ester A mixture of 3-bromo-6-chloro-4-(4-tert-butoxycarbonyl-3-butenyl)indole-2-carboxylic acid methyl ester (4.0 g, 9.03 mmol), triphenylphosphune (0.711 g, 2.71 mmol), triethylamine (3.78 mL, 27.1 mmol), and palladium(II) acetate (0.203 g, 0.903 mmol) in DMF (40 mL) was stirred for 5 h at 80° C., diluted with water, and extracted with ethyl acetate. The extract was washed with water and brine, dried over $MgSO_4$, and concentrated. The residue was partially purified by silica gel column chromatography with 8:1 hexane/ethyl acetate to give 2.56 g of the crude title compound, which was further purified by silica gel column cromatography with toluene to give 1.11 g of the title compound (34%): $^1H$ NMR ($CDCl_3$) δ8.95 (bs, 1H), 7.17 (s, 1H), 6.87 (s, 1H), 3.96 (s, 3H), 3.88 (m, 1H), 3.02 (m, 1H), 2.82 (dt, 1H, J=16.8, 2.8 Hz), 2.66 (dd, 1H, J=14.5, 3.6 Hz), 2.38 (dd, 1H, J=14.5, 11.2 Hz), 2.19 (m, 1H), 1.99 (m, 1H).

12) 7-Chloro-3-tert-butoxycarbonylmethyl-1,3,4,5-tetrahydrobenz[cd]indole-2-carboxylic acid methyl ester A solution of 7-chloro-3-tert-butoxycarbonylmethylene-1,4,5-trihydrobenz[cd]indole-2-carboxylic acid methyl ester (110 mg, 0.276 mmol) in toluene (3 mL) was hydrogenated under 70 atom of hydrogen at room temperature for 4 days in the presence of tris(triphenylphosphine)chlororhodium (51 mg). The solvent was evaporated and the residue was purified by silica gel column chromatography with 10:1 hexane/ethyl acetate to give 54 mg of the title compound (63%): $^1H$ NMR ($CDCl_3$) δ8.81 (bs, 1H), 7.17 (s, 1H), 6.87

(s, 1H), 3.96 (s, 3H), 3.88 (m, 1H), 3.02 (m, 1H), 2.82 (d1H, J=16.8, 2.8 Hz), 2.66 (dd, 1H, J=14.5, 3.6 Hz), 2.38 (dd, 1H, J=14.5, 11.2 Hz), 2.19 (m, 1H), 1.99 (m, 1H), 1.48 (s, 9H).

Example 10

7-Chloro-3-carboxymethyl-1,3,4,5-tetrahydrobenz[cd]indole-2-carboxylic acid methyl ester A mixture of 7-chloro-3-tert-butoxycarbonylmethyl-1,3,4,5-tetrahydrobenz[cd]indole-2-carboxylic acid methyl ester (54 mg, 0.148 mmol) and p-toluenesulfonic acid (3 mg) in toluene (1 mL) was refluxed for 1 h, diluted with ethyl acetate, washed with water and brine, dried over MgSO4, and concentrated to give 52 mg of the title compound (quant): $^1$H NMR (DMSO-$d_6$) δ12.17 (bs, 1H), 11.60 (s, 1H), 7.17 (s, 1H), 6.84 (s, 1H), 3.88 (s, 3H), 3.77 (m, 1H), 2.94 (mt, 1H, J=13.9 Hz), 2.80 (md, 1H, J=17.2 Hz), 2.56 (dd, 1H, J=15.2, 4.3 Hz), 2.37 (dd, 1H, J=15.2, 10.6 Hz), 2.11 (md, 1H, J=12.5 Hz), 1.88 (m, H).

What is claimed is:

1. A tricyclic indole-2-carboxylic acid derivative represented by the formula 1:

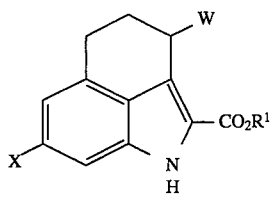

wherein

X represents an alkyl, halogen or cyano;

R$^1$ represents hydrogen, or a protecting group of carboxyl group;

W represents hydrogen, —CO$_2$R$^{3i}$, —CONR$^{3i}$R$^{4i}$, —A—CO$_2$R$^{3i}$ or —A—CONR$^{3i}$R4i, wherein —A— represents an alkylene group containing from 1 to 2 carbon atoms and R$^{3i}$ and R$^{4i}$ independently represent hydrogen, an alkyl group containing from 1 to 6 carbon atoms, an aryl group containing from 6 to 10 carbon atoms, or a substituted C$_{6-10}$ aryl group wherein the substituent on the aryl is selected from the group consisting of alkyl, halogen, —Y—J, or —Z—E, wherein J represents an acidic group which is readily deprotonated in vivo to provide an anion, or a group which is convertible thereto in vivo by hydrolysis, E represents a basic group which is readily protonated in vivo to produce a cation, or a group which is convertible thereto in vivo by hydrolysis, Y represents a single bond, a C$_{1-6}$ alkylene, a C$_{2-6}$ alkenylene, a substituted C$_{1-6}$ alkylene or Y$^1$—Q—Y$^2$, wherein Y$^1$ represents a single bond or a C$_{1-6}$ alkylene, Y$^2$ represents a C$_{1-6}$ alkylene, and Q represents a heteroatom selected from oxygen or sulfur, and Z represents a C$_{1-6}$ alkylene; wherein the substituent of the term "substituted alkylene" for Y is selected from the group consisting of hydroxy, —OR$^{3s}$, —OCOR$^{3s}$, amino, —NHCOR$^{3s}$, —NHCO$_2$R$^{3s}$, carboxy, and —CO$_2$R$^{3s}$, wherein R$^{3S}$ represents alkyl or C$_{3-6}$ alkenyl or a pharmaceutically acceptable salt thereof.

2. A compound according to claim 1, wherein X is halogen.

3. A compound according to claim 2, wherein W is —A—CO$_2$R$^{3i}$.

4. A compound according to claim 3, wherein —A— is methylene.

5. A compound according to claim 4, wherein R$^{3i}$ is hydrogen.

6. A compound according to claim 2, wherein W is —A—CONR$^{3i}$R$^{4i}$.

7. A compound according to claim 6, wherein —A— is methylene.

8. A compound according to claim 7, wherein R$^{3i}$ is hydrogen and R$^{4i}$ is an aryl or a substituted aryl.

9. A compound according to claim 5, wherein R$^1$ is hydrogen.

10. A compound according to claim 8, wherein R$^1$ is hydrogen.

11. A compound according to claim 10, wherein the number of substituents of the substituted aryl is two.

12. A compound according to claim 7, wherein —NR$^{3i}$R$^{4i}$ is a group represented by formula 2:

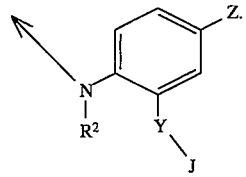

wherein R$^2$ represents hydrogen or an alkyl having not more than 6 carbon atoms, and J, E, Y and Z are the same as defined in claim 1.

13. A compound according to claim 1, wherein J is selected from the group consisting of carboxyl, tetrazolyl, —COOR$^{3J}$, —CONH$_2$, —CON(OH)H, —CONHR$^{3J}$, —CON(OH)R$^{3J}$, —CON(OR$^{5J}$)R$^{3J}$ and —CONR$^{3J}$R$^{4J}$, wherein R$^{3J}$ and R$^{4J}$ independently represent alkyl and alkenyl, or R$^{3J}$ and R$^{4J}$ are joined to form a cyclic amine together with the nitrogen atom, and R$^{5J}$ represents alkyl; E is selected from the group consisting of —NH$_2$, —NHR$^{3E}$, —NR$^{3E}$R$^{4E}$, —NH—C(=NH)—NH$_2$, —NH—C(=NH)—NHR$^{3E}$, —NH—C(=NH)—NR$^{3E}$R$^{4E}$, —NHL, —NLR$^{3E}$, —NH—C(=NL)—NH$_2$, —NH—C(=NL)—NHR$^{3E}$, and —NH—C(=NL)—NR$^{3E}$R$^{4E}$, wherein R$^{3E}$ and R$^{4E}$ independently represent a group selected from the group consisting of alkyl, and alkenyl, or R$^{3E}$ and R$^{4E}$ are joined to form a cyclic amine together with the nitrogen atom; L is a group selected from the group consisting of alkanoyl and alkoxycarbonyl; wherein the term "alkenyl" means an alkenyl group containing from 3 to 6 carbon atoms, of which an olefinic carbon atom is not connected directly with the nitrogen atom; the term "alkyl" means an alkyl group containing from 1 to 6 carbon atoms; the term "cyclic amine" which R$^{3E}$ and R$^{4E}$, or R$^{3J}$ and R$^{4J}$ are joined to form includes 3 to 7 membered cyclic amine; the term "alkanoyl" means an alkanoyl group containing from 1 to 6 carbon atoms; and the term "alkoxycarbonyl" means an alkoxycarbonyl group containing from 2 to 6 carbon atoms.

14. A compound according to claim 13, wherein R$^1$ is selected from a group consisting of hydrogen, substituted or unsubstituted alkyl containing from 1 to 6 carbon atoms, benzyl, p-methoxybenzyl and p-nitrobenzyl, wherein the substituent on the alkyl is selected from the group consisting of alkoxy containing from 1 to 6 carbon atoms, alkanoyloxy containing from 1 to 6 carbon atoms, and aroyloxy containing up to 11 carbon atoms.

15. A pharmaceutical composition comprising a pharmaceutically effective amount of a compound of claim 1 or a pharmaceutically acceptable salt thereof and a pharmaceutically acceptable carrier or diluent.

16. A method for treating central nervous system damage in a patient which is induced by an ischemic or hypoxic condition, which comprises administering a pharmaceutically effective amount of a compound of claim 1 or a pharmaceutically acceptable salt thereof to said patient.

17. A method for treating a neurodegenerative disorder in a patient which comprises administering a pharmaceutically effective amount of a compound of claim 1 or a pharmaceutically acceptable salt thereof to said patient.

18. A method for producing an analgetic, antidepressant, anxiolitic, or anti-schizophrenic effect in a patient, which comprises administering a pharmaceutically effective amount of a compound of claim 1 or a pharmaceutically acceptable salt thereof to said patient.

19. A method for treating epilepsy or stroke which comprises administering a pharmaceutically effective amount of a compound of claim 1 or a pharmaceutically acceptable salt thereof to a patient.

* * * * *